US012612641B2

(12) United States Patent
Tang et al.

(10) Patent No.: US 12,612,641 B2
(45) Date of Patent: Apr. 28, 2026

(54) RICE MALE FERTILITY REGULATORY GENE, MUTANT OF RICE MALE FERTILITY REGULATORY GENE, USE THEREOF AND A METHOD FOR REGULATING RICE FERTILITY

(71) Applicant: HAINAN BOLIAN TECHNOLOGY CO., LTD., Hainan (CN)

(72) Inventors: Jie Tang, Hainan (CN); Tuan Long, Hainan (CN); Chunyu Wu, Hainan (CN); Jialin Li, Hainan (CN); Hao Liu, Hainan (CN); Yanqun Li, Hainan (CN); Xiaobin Han, Hainan (CN); Xinpeng Li, Hainan (CN); Baoguang An, Hainan (CN); Xiang Zeng, Hainan (CN); Yongzhong Wu, Hainan (CN); Peijin Huang, Hainan (CN)

(73) Assignee: Hainan Bolian Technology Co., Ltd., Hainan (CN)

( * ) Notice: Subject to any disclaimer, the term of this patent is extended or adjusted under 35 U.S.C. 154(b) by 650 days.

(21) Appl. No.: 17/927,343

(22) PCT Filed: Dec. 17, 2020

(86) PCT No.: PCT/CN2020/137145
§ 371 (c)(1),
(2) Date: Nov. 22, 2022

(87) PCT Pub. No.: WO2021/244007
PCT Pub. Date: Dec. 9, 2021

(65) Prior Publication Data
US 2023/0220413 A1     Jul. 13, 2023

(30) Foreign Application Priority Data
Jun. 2, 2020    (CN) .......................... 202010491100.4
Jun. 2, 2020    (CN) .......................... 202010491115.0

(51) Int. Cl.
*C12N 15/82*    (2006.01)
*C07K 14/415*    (2006.01)

(52) U.S. Cl.
CPC ........ *C12N 15/8289* (2013.01); *C07K 14/415* (2013.01)

(58) Field of Classification Search
None
See application file for complete search history.

(56) References Cited

U.S. PATENT DOCUMENTS

2004/0123343 A1     6/2004    La Rosa

FOREIGN PATENT DOCUMENTS

CN     105002191 A    10/2015
CN     110511945 A    11/2019

OTHER PUBLICATIONS

Liu W, Shahid MQ, Bai L, Lu Z, Chen Y, et al. (2015) Evaluation of Genetic Diversity and Development of a Core Collection of Wild Rice (*Oryza rufipogon Griff.*) Populations in China. PLOS One 10(12): e0145990; Published Dec. 31, 2015 (Year: 2015).*
Shah et al. Predicting Enzyme Function from Sequence: A Systematic Appraisal. Proc Int Conf Intell Syst Mol Biol. 1997 ; 5: 276-283; Published 1997 (Year: 1997).*
Joshi et al. Quantitative assessment of relationship between sequence similarity and function similarity BMC Genomics 2007, 8:222 ; Published Jul. 9, 2007 (Year: 2007).*
Chen and Liu, 2014, Male sterility and fertility restoration in crops, Annu Rev Plant Biol, 65: 579-606.
Zhou H, et al, 2014, RNase ZS1 processes UbL40 mRNAs and controls thermosensitive genic male sterility in rice, Nature Communications, 5: 4884-4892.
Ma X, et al. A Robust CRISPR-Cas9 System for Convenient, High-Efficiency Multiplex Genome Editing in Monocot and Dicot Plants. Mol Plant, 2015, 8: 1274-84.
Yu, J. et al., EAY95238.1 Genbank, Mar. 23, 2015 (Mar. 23, 2015) Origin, CDS.
XP_020880420.1 Genbank, May 11, 2017 (May 11, 2017) Origin, CDS.
MORNY9 UniProtKB, Apr. 3, 2013 (Apr. 3, 2013) Sequence.
XP_006652672.1 Genbank, Mar. 4, 2016(Mar. 4, 2016) Origin, CDS.
XP_002448368.1 Genbank, Jun. 13, 2017(Jun. 13, 2017) Origin, CDS.
NP_001151356.2 Genbank, Sep. 8, 2017(Sep. 8, 2017) Origin, CDS.
XT_009382277.1 Genbank, Oct. 25, 2016(Oct. 25, 2016) Origin, CDS.

(Continued)

*Primary Examiner* — Anne Kubelik
*Assistant Examiner* — Keith R. Williams
(74) *Attorney, Agent, or Firm* — Levine Bagade Han LLP

(57)    ABSTRACT

The present invention relates to the technical field of biology, in particular to a rice male fertility regulatory gene, the use thereof and a method for regulating rice fertility by means of using CRISPR-Cas9, and a mutant of the rice male fertility regulatory gene and a molecular marker and the use thereof. The present invention provides a rice gene GMS2 with the functions of regulating male germ cell development in rice and pollen fertility. The mutant of a rice male fertility regulatory protein GMS2 provided by the present invention can make rice pollen completely sterile, resulting in rice male sterility. The rice gene GMS2 and the mutant thereof, provided by the present invention, can be used in the sterile seed production and manufacturing of rice hybrids, thereby possessing both great application value and economic value.

4 Claims, 13 Drawing Sheets

Specification includes a Sequence Listing.

(56)  References Cited

OTHER PUBLICATIONS

Nyima, T. et al., KAE8775436.1 Genbank, Nov. 29, 2019(Nov. 29, 2019) Origin, CDS.

Alexandrov, N.N. et al., ACG42498.1 Genbank, Dec. 10, 2008(Dec. 10, 2008) Origin, CDS.

XP 004976555.1 Genbank, Oct. 13, 2017(Oct. 13, 2017) Origin, CDS.

XM_015778561.2 Genbank, Aug. 7, 2018(Aug. 7, 2018) Origin, CDS.

Kikuchi, S. AK241942.1 Genbank, Dec. 4, 2008(Dec. 4, 2008) Origin, CDS.

Jun Li et al., "The fasciclin-like arabinogalactan protein gene, FLA3, is involved in microspore development of *Arabidopsis*," The Plant Journal, Sep. 28, 2010 (Sep. 28, 2010) Issue.3, vol. 64, 482-497.

Sun-Ju Rhee et al., "De Novo-based Transcriptome Profiling of Male-sterile and Fertile Watermelon Lines," PLOS One, Nov. 2, 2017 (Nov. 2, 2017), Issue.11, vol. 12, 1-17.

Altschul, Stephen F. et al., "Basic Local Alignment Search Tool," J Mol Biol, 215(3): 403-410, 1990.

International Search Report for counterpart International Application No. PCT/CN2020/137145, filed Dec. 17, 2020, mailed Feb. 26, 2021 with English translation, 11 pages.

Written Opinion of International Searching Authority for counterpart International Application No. PCT/CN2020/137145, filed Dec. 17, 2020, mailed Feb. 26, 2021 with English translation, 13 pages.

International Preliminary Report on Patentability for counterpart International Application No. PCT/CN2020/137145, filed Dec. 17, 2020, mailed Dec. 6, 2022, 7 pages.

XP_009382277.1 Genbank, Oct. 25, 2016 (Oct. 25, 2016) Origin, CDS.

* cited by examiner

Detection of F3 population (3148/MH63) with InD48490

Figure 8A
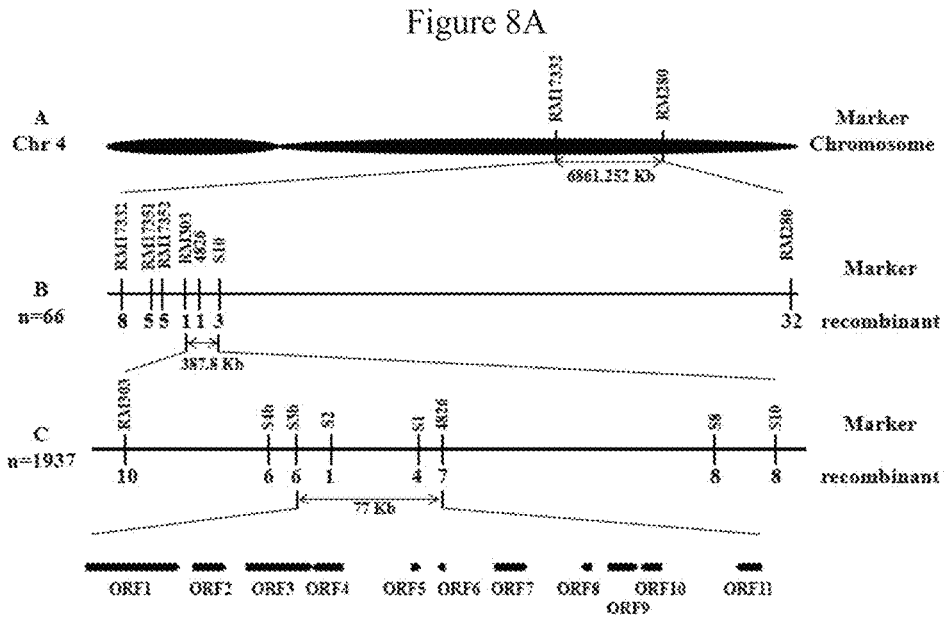
Figure 8B
$$TAC\ (AACAGCTAC)_{118}CTC \longrightarrow TAC(-)_{118}CTC$$
$$Asn_{40}Ser_{41}Tyr_{42} \longrightarrow \mbox{}^-_{40}$$
■ Coding region
M3148 (GMS2)
Figure 9

Figure 10
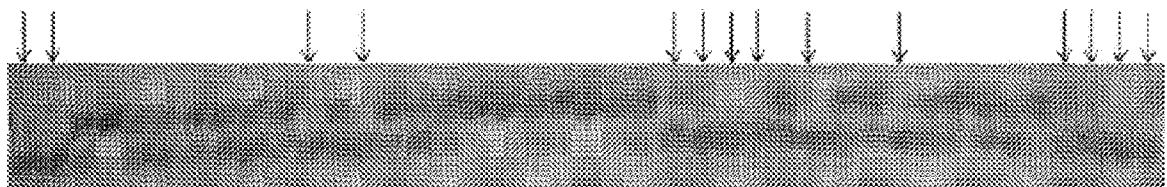
Figure 11
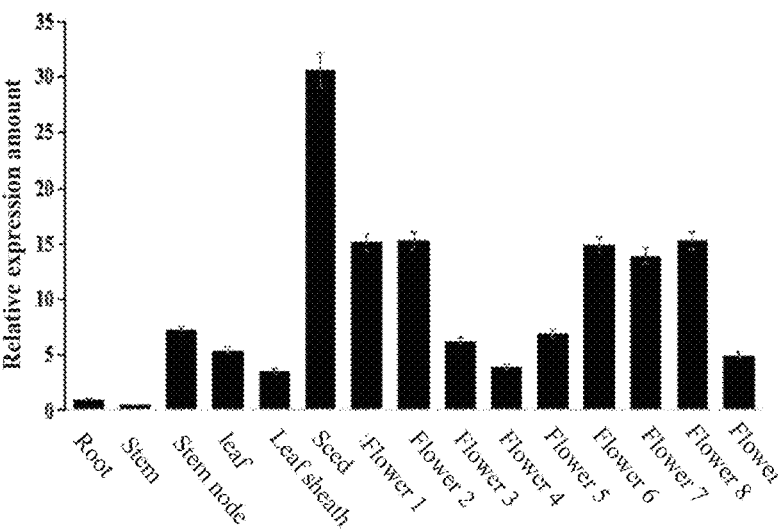
Figure 12

Expression analysis of 3148OX

RICE MALE FERTILITY REGULATORY GENE, MUTANT OF RICE MALE FERTILITY REGULATORY GENE, USE THEREOF AND A METHOD FOR REGULATING RICE FERTILITY

CROSS-REFERENCE TO RELATED APPLICATIONS

The present application is a US national phase application under 35 USC § 371 of International Application No. PCT/CN2020/137145, filed Dec. 17, 2020, and claims priority to Chinese Patent Application No. 202010491115.0, entitled "Mutant of Rice Male Fertility Regulatory Gene, and Molecular Marker and Use thereof", filed on Jun. 2, 2020, and Chinese Patent Application No. 202010491100.4, entitled "Rice Male Fertility Regulatory Gene, Uses thereof, and Method for Regulating Rice Fertility Using CRISPR-Cas9", filed on Jun. 2, 2020, the entire disclosures of which were incorporated herein by reference in their entireties.

INCORPORATION BY REFERENCE

This patent application incorporates by reference the sequence listing identified as KHP2131102358_amended_sequence_listing_1.txt, which is an ASCII text file in computer readable form created Nov. 22, 2022, having a file size of 60,993 bytes.

TECHNICAL FIELD

The present invention relates to the field of biology, specifically to a plant fertility regulatory gene GMS2, a GMS2-encoded protein, a GMS2 gene knockout mutant, and uses of the GMS2 gene, the protein and the mutant in hybridization breeding: as well as a mutant of the plant fertility related protein GMS2, a coding gene of the mutant, a molecular marker thereof and uses thereof in hybridization breeding.

BACKGROUND ART

Rice (*Oryza sativa* L.) is one of the most important food crops in the world. With the growth of population and the improvement of living quality, it is estimated that the annual output of rice will increase 1-2 times to meet the needs of human development by 2050. Hybrid rice is the first generation of offspring obtained from the hybridization between parents, and its yield is often increased by 15% or more compared with that of the conventional rice parents, and its resistance and adaptability are also far better than those of the parents. Therefore, the application and promotion of hybrid rice is an important way to improve rice yield.

Male sterile line is the key node of hybrid rice breeding technology. Male sterile line refers to a plant line in which male gamete develops abnormally and loses fertility, while female gamete develops normally. It can only act as a female parent to receive pollen from a male parent, and cannot bear fruit by self-fertilization. At present, there are two types of male sterile lines applied in hybrid rice production, i.e., the cytoplasm-nucleolus interacting type and the photo-thermo-sensitive type. The sterility gene of the cytoplasm-nucleolus interacting type male sterile line is in the cytoplasm, and there is no fertility restorer gene in the nucleus. Fertile F1 hybrids can be produced when a restorer line having a fertility restorer gene in the nucleus is combined and hybridized with the cytoplasm-nucleolus interacting type male sterile line, and sterile line seeds can be propagated when a maintainer line having no fertility restorer gene in the nucleus and no sterile gene in the cytoplasm is hybridized with the cytoplasm-nucleolus interacting type male sterile line. This hybrid rice breeding technology is often referred to as the "three-line method" due to the need for a three-line combination of a sterile line, a maintainer line and a restorer line. Some genes that control cytoplasm-nucleolus interacting type sterility and the corresponding fertility restoration have been cloned (Chen and Liu, 2014, Malesterity and Fertility Restoration in Crops, Annu Rev Plant Biol, 65:579-606). The cytoplasm-nucleolus interacting type sterility line is the first sterile line that has been applied in large-scale in hybrid rice breeding, which has laid a material foundation for the establishment and development of hybrid rice industry. However, due to the combination of the cytoplasm-nucleolus interacting type sterility line is restricted by the genotype of restorer line, only about 5% of the germplasm resources can be utilized. However, the cytoplasmic sterility genes have the potential risk of causing poor rice quality and epidemic of certain diseases and insect pests.

The photo-thermo-sensitive-type male sterile line is a sterile line with fertility regulated by light and temperature environment. Under certain light and temperature conditions, the sterile line remains sterile and can be used for combination hybridization. The fertility of the sterile line restores when conditions change, and the sterile line can be used for sterile line propagation. Since the photo-thermo-sensitive male sterile line realizes the integration of the sterile line and the maintainer line, only the male parent is required to be combined with the photo-thermo-sensitive-type male sterile line to produce a first-generation hybrid, the corresponding breeding technology is often referred to as the "two-line method". The genes that regulate photo-thermo-sensitive-type male sterility are in the nucleus, and the genes that have been cloned at present include PMS3, TMS5, CSA and TMS10 (Chen and Liu, 2014, Male sterility and fertility restoration in crops, Annu Rev Plant Biol, 65:579-606; and Zhou H, et al, 2014, RNase ZS1 processes UbL40 mRNAs and controls thermosensitive genic male sterility in rice, Nature Communications, 5:4884-4892). Compared with the cytoplasm-nucleolus interacting type sterility line, the photo-thermo-sensitive-type sterile line has a simple breeding program and is more free in combination due to the wide existence of restorer genes. The large-scale application of the photo-thermo-sensitive sterile line has greatly consolidated and promoted the development of hybrid rice industry. However, because the fertility of the type of sterile line is affected by the light and temperature environment, it also leads to high risk of seed production and limited seed production area.

In order to overcome the key defects in the current hybrid rice breeding technology, the creation and utilization of new types of sterile lines will be an important breakthrough. Nuclear male sterility is resulted from mutation of the nuclear gene, and there are dominant and recessive mutations, and gene mutations in the sporophyte and gametophyte. Dominant gene mutations and gametophytic gene mutations can only be inherited through female gamete, while recessive mutations can be inherited through either female or male gamete, and such inheritance follows Mendel's law. The present invention provides a plant fertility-related regulatory gene and a male sterile line of a recessive nuclear sterile type generated based on mutation of the gene. The male sterile line has stable fertility, which is only regulated by a single nuclear coding gene and is not affected by light and temperature environment. The fertility restorer gene of the sterile line is widely present in rice germplasm resources, and fertility can also be restored by transferring wild-type genes. The gene and the sterile line generated by mutation of the gene provide elements for researching and developing a novel hybrid breeding and seed production technology of rice, and lay a foundation for solving the problems existing in the prior art.

SUMMARY OF THE PRESENT INVENTION

One purpose of the present invention is to provide a plant fertility-related protein, a gene encoding the same, and use thereof in regulating male fertility of a plant by manipulating the gene. By way of non-limiting example, any of the methods described below may be used with the corresponding nucleotide sequences of the plant fertility related protein provided by the present invention, for example, mutating an endogenous coding sequence of said plant fertility related protein in a plant, introducing an antisense sequence of said sequence into a plant, using a hairpin format, or linking it to other nucleotide sequences so as to regulate the phenotype of the plant, or any of a variety of methods known to a person skilled in the art that may be used to affect the male fertility of the plant.

In the present invention, a pollen development regulatory gene GMS2 with a male fertility regulation function is found in rice. GMS2 is located on rice chromosome 4, and its genomic nucleotide sequence in *japonica* rice variety Nipponbare is represented by SEQ ID NO: 1, the CDS sequence (coding DNA sequence) is represented by SEQ ID NO: 2, and the amino acid sequence is represented by SEQ ID NO: 3. In the indica rice variety 9311, genomic nucleotide sequence of the fertility gene is represented by SEQ ID NO: 4, its CDS sequence is represented by SEQ ID NO: 69, and its amino acid sequence is identical to that of the *japonica* rice variety Nipponbare. The amino acid sequence of the fertility gene in *Arabidopsis lyrata* is represented by SEQ ID NO: 9; the amino acid sequence of the fertility gene in banana (*Musa acuminata*) is represented by SEQ ID NO: 10; the amino acid sequence of the fertility gene in *Oryza glaberrima* is represented by SEQ ID NO: 11: the amino acid sequence of the fertility gene in *Oryza brachyantha* is represented by SEQ ID NO: 12: the amino acid sequence of the fertility gene in barley (*Hordeum vulgare*) is represented by SEQ ID NO: 13: the amino acid sequence of the fertility gene in *sorghum* (*Sorghum bicolor*) is represented by SEQ ID NO: 14; the amino acid sequence of the fertility gene in maize (*Zea mays*) is represented by SEQ ID NO: 15; and the amino acid sequence of the fertility gene in millet (*Setaria italica*) is represented by SEQ ID NO: 16.

The fertility gene describe above may be isolated from various plants. It should be understood by a person skilled in the art that the fertility gene of the present invention includes a highly homologous functional-equivalent sequence that is highly homologous to the GMS2 gene and has the same fertility regulation function. The highly homologous functional-equivalent sequence includes a DNA sequence capable of hybridizing with the nucleotide sequences of the GMS2 gene disclosed by the present invention under stringent conditions. The "stringent conditions" used in the present invention are well known and include for example hybridization in a hybridization solution containing 400 mM NaCl, 40 mM PIPES (pH6.4) and 1 mM EDTA at 60° C. for 12 to 16 hours, followed by washing with a washing solution containing 0.1% SDS and 0.1×SSC at 65° C. for 15 to 60 minutes.

The functional-equivalent sequence also includes a DNA sequence having at least 85%, 90%, 95%, 96%, 97%, 98%, or 99% sequence similarity with the nucleotide sequence of the GMS2 gene disclosed by the present invention and having fertility regulation function, which may be isolated from any plant. Among them, the percentage of sequence similarity may be obtained by well-known bioinformatics algorithms including Myers and Miller algorithm (Bioinformatics, 4 (1): 1117, 1988), Needleman-Wunsch global alignment method (J Mol Biol, 48 (3): 443-453, 1970), Smith-Waterman local comparison method (J Mol Biol, 147:195-197, 1981), Pearson and Lipman similarity search method (PNAS, 85 (8): 2444-2448, 1988), and Karlin and Altschule algorithm (Altschule et al., J Mol Biol, 215 (3): 403-410, 1990; and PNAS, 90:5873-5877, 1993). This is familiar to a person skilled in the art.

Based on the above findings of the present invention, a first aspect of the present invention is to provide a plant male fertility-related protein, which is the protein described in (1) or (2) below:

(1) a protein having an amino acid sequence represented by SEQ ID NOs: 3, 9, 10, 11, 12, 13, 14, 15 or 16;

(2) a protein with the activity of regulating plant male fertility obtained by substitution and/or deletion and/or addition of one or more amino acid residues in SEQ ID NOs: 3, 9, 10, 11, 12, 13, 14, 15 or 16.

The present invention provides a nucleic acid encoding the plant male fertility related protein.

The nucleic acid of the present invention may be isolated and obtained from any plant, including but not limited to, *Brassica*, maize, wheat, *sorghum* (*Sorghum bicolor*), *Oryza brachyantha, Oryza glaberrima, Brachypodium, Crambe, Brassica* alba, Castor bean (*Ricinus communis L.*), sesame, cottonseed, linseed, soybean, *Arabidopsis, Phaseolus* Linn, peanut, *Lotus corniculatus L.*, oat, rapeseed, barley, Rye (*Secale cereale L.*), millet, Milo (*Sorghum Moench*), triticale, einkorn (*Triticum monococcum*), Spelt, emmer (*Triticum dicoccum*), flax, Gramma grass, *Tripsacum, Euchlaena mexicana, Festuca ovina L.*, Perennial wheatgrass, Coriander, *Vaccinium oxycoccos* Linn, papaya, banana, safflower, oil palm, cantaloupe, apple, cucumber, dendrobium, *gladiolus, chrysanthemum*, plants of the lily family (*Liliaceae*), cotton (*Gossypium* spp), sunflower, *Brassica campestris*, sugar beet (*Beta vulgaris* L), coffee, ornamental plants and conifer and the like. Preferably, the plants include maize, millet, *Arabidopsis thaliana, Brachypodium distachyon*, soybean, safflower, mustard, wheat, barley, Rye (*Secale cereale L.*), *Oryza brachyantha, Oryza glaberrima*, cotton, and *sorghum* (*Sorghum bicolor*).

Taking rice as an example, the sequence of the nucleic acid is any of the follows:

(1) a nucleic acid having a nucleotide sequence represented by SEQ ID NO: 1 or 2;

(2) a nucleic acid having a nucleotide sequence represented by SEQ ID NO: 4 or 69;

(3) a DNA fragment capable of hybridizing with the DNA of any one of the sequences in (1) or (2) under stringent conditions;

(4) a DNA fragment complementary to any one of the sequences in (1) or (2);

(5) a DNA fragment capable of affecting the fertility of plant pollen formed by substitution and/or insertion and/or deletion of one or more bases or insertion/deletion/translocation/inversion of a nucleotide sequence of a large fragment based on any one of the sequences in (1) or (2);

(6) a DNA fragment having 85%, 90%, 95%, 96%, 97%, 98% or 99% or more identity with the DNA fragment of any one of the sequences in (1) or (2) and encoding a rice male fertility related protein.

The present invention provides an inhibitory factor of a nucleic acid encoding the plant male fertility related protein, and the introduction of the inhibitory factor into a plant can result in reduced expression level, non-expression or mutation-induced inactivation of the nucleic acid encoding the plant male fertility related protein. The inhibitory factor may be a protein or a nucleic acid (including but not limited to antisense genes, siRNA and DNA thereof, dsRNA and DNA thereof, sgRNA and DNA thereof, and the like).

The present invention provides a biological material comprising a nucleic acid encoding the plant male fertility related protein, or comprising an inhibitory factor of the nucleic acid encoding the plant male fertility related protein, and the biological material is an expression cassette, a vector, a host cell, a transgenic cell line or a transgenic plant.

The present invention provides a plant, plant tissue, or plant cell exhibiting a male sterility trait results from a mutation of the nucleic acid encoding the plant male fertility related protein, and the mutation is deletion, insertion, or substitution mutation of one or more nucleotides, or a mutation generated by the transformation of an antisense gene, co-suppression or introduction of a hairpin structure: the mutation results in reduced expression, non-expression or inactivation of the plant male fertility related protein.

The plant, plant tissue or plant cell may be obtained by natural mutation or artificial mutagenesis, and may be a transgenic plant, plant tissue or plant cell or may be a non-transgenic plant, plant tissue or plant cell.

The artificial mutagenesis includes physical and chemical mutagenesis, insertion mutation, gene targeting knockout, transformation, cosuppression of an antisense gene or introduction of a hairpin structure, and the like.

The plant includes, but is not limited to, *Brassica*, maize, wheat, *sorghum (Sorghum bicolor)*, *Oryza brachyantha, Oryza glaberrima, Brachypodium, Crambe, Brassica* alba, sesame, soybean, *Arabidopsis, Phaseolus* Linn, peanut, *Lotuscorniculatus L*, oat, rapeseed, barley, Rye (*Secale cereale L.*), millet, Milo (*Sorghum Moench*), triticale, einkorn (*Triticum monococcum*), Spelt, emmer (*Triticum dicoccum*), flax, Gramma grass, *Tripsacum, Euchlaena mexicana, Festuca ovina L*, Perennial wheatgrass, Coriander, *Vaccinium oxycoccos* Linn, papaya, banana, safflower, oil palm, cantaloupe, apple, cucumber, dendrobium, *gladiolus, chrysanthemum*, plants of the lily family (*Liliaceae*), cotton, sunflower, *Brassica campestris*, sugar beet, coffee, ornamental plants and conifer and the like. Preferably, maize, millet, *Arabidopsis thaliana, Brachypodium distachyon*, mustard, wheat, barley, Rye (*Secale cereale L.*), *Oryza brachyantha, Oryza glaberrima*, cotton, and *sorghum (Sorghum bicolor)* are included.

Optionally, the plant, plant tissue, or plant cell is obtained by the CRISPR-Cas9 method using a target sequence located in a sequence of a nucleic acid encoding the plant male fertility related protein, and the reverse complementary sequence of the target sequence has a 5'-(N) X-NGG-3' structure, wherein N represents any one of A, T, C and G, and X is any nucleotide sequence of 19nt or 20nt.

Specifically, the plant, plant tissue, or plant cell derived line is a plant with mutation at a target site or in an area adjacent to the target site obtained by using CRISPR-Cas9 method with GCGGTCGGTGGCGGCCATGG (SEQ ID NO: 17) and CGCCTCCCTCGCCGTCGCGG (SEQ ID NO: 18) as target sites.

A second aspect of the present invention provides any of the following uses of the plant male fertility related protein or a nucleic acid encoding the plant male fertility related protein or an inhibitory factor of the nucleic acid or the biological material or the plant, plant tissue or plant cell:

(1) use in regulating plant male fertility;

(2) use in preparing male sterile plants;

(3) use in restoring the male fertility of recessive nuclear sterility caused by mutation of the nucleic acid encoding the plant male fertility related protein;

(4) use in plant hybridization breeding;

(5) use in the improvement of plant germplasm resources.

In the above (1), regulating the plant male fertility may reduce or lose the plant male fertility. Specifically, it may be implemented by regulating the development of plant male germ cells and pollen. Among them, the reduction or loss of male fertility in a plant may be implemented by mutating the gene encoding the plant male fertility related protein in a plant so that the protein has reduced expression level or no expression, or by introducing an inhibitory factor of a nucleic acid encoding the plant male fertility related protein into the plant.

In the above (2), the male sterile plant is a recessive genic male sterile line with a homozygous mutation of a nucleic acid encoding the plant male fertility related protein.

In the above (3), the male fertility of a plant with recessive genic male sterility due to mutation or inactivation of the plant male fertility related protein is restored by introducing a nucleic acid encoding the plant male fertility related protein into the plant so that a foreign gene is introduced to obtain a high-quality transgenic crop.

In the above (4), hybridization breeding and seed production are performed using a recessive genic male sterile line with a homozygous mutation of a nucleic acid encoding the plant male fertility related protein.

In the above (5), the improvement includes yield improvement, quality improvement, pest and disease resistance, stress resistance, lodging resistance, and the like.

The plants described above are self-pollinated or cross-pollinated plants including, but not limited to, rice, maize, wheat and *sorghum (Sorghum bicolor)*.

A third aspect of the present invention is to provide a method for affecting plant fertility by affecting the plant male fertility-related protein or the sequence of a nucleic acid encoding the protein, or by affecting transcription, translation of the nucleic acid. Said affecting plant fertility refers to altering the fertility of the plant, such as causing male sterility of the plant. Specifically, depending on the requirements of practical application, the plant male fertility related protein or the sequence of a nucleic acid encoding the protein or the expression and translation thereof in plants may be affected by a variety of methods to achieve the effect of regulating the male fertility of plants. More specifically, affecting the plant male fertility related protein or the sequence of a nucleic acid encoding the protein or the expression and translation thereof in plants may be performed using a number of tools available to a person skill in the art, for example, physical and chemical mutagenesis, insertion mutation, gene targeting knockout, transformation, co-suppression of an antisense gene or introduction of a hairpin structure, and the like, may be used to disrupt the normal expression of the plant male fertility related protein, thereby obtaining a male-sterile plant.

A fourth aspect of the present invention is to provide a mutant of the plant male fertility related protein, which is obtained by insertion, and/or deletion, and/or substitution of several nucleotides in the gene encoding the plant male fertility related protein, the mutant is capable of causing male sterility in rice.

The present invention provides a target site suitable for targeted knockout of a nucleic acid encoding the plant fertility related protein by CRISPR-Cas9 method, which is target site 1: GCGGTCGGTGGCGGCCATGG (SEQ ID NO: 17) and/or target site 2: CGCCTCCCTCGCCGTCGCGG (SEQ ID NO: 18).

The present invention also provides a sgRNA specifically targeting to the target site 1 and the target site 2 as described above.

A CRISPR-Cas9 targeting vector containing the DNA sequence of the above sgRNA is also within the scope of protection of the present invention.

A fifth aspect of the present invention is to provide any of the following uses of the target site or the sgRNA targeting to the target site or the CRISPR-Cas9 targeting vector containing the DNA of the sgRNA:

(1) use in regulating plant male fertility;
(2) use in preparing male sterile plants;
(3) use in plant hybridization breeding;
(4) use in the improvement of plant germplasm resources.

In the above (1), regulating the plant male fertility may reduce or lose the plant male fertility. Specifically, it may be implemented by regulating the development of plant male germ cells and pollen. Among them, the reduction or loss of male fertility in a plant may be implemented by mutating the gene encoding the plant male fertility related protein in a plant so that the protein has reduced expression level or no expression, or by introducing an inhibitory factor of a nucleic acid encoding the plant male fertility related protein into the plant.

In the above (2), the male sterile plant is a recessive genic male sterile line with a homozygous mutation of a nucleic acid encoding the plant male fertility related protein.

In the above (3), using the inhibitory factor of the nucleic acid to inactivate the fertility regulatory protein, thereby creating a recessive genic male sterile plant for hybridization breeding and seed production.

In the above (4), the improvement includes yield improvement, quality improvement, pest and disease resistance, stress resistance, lodging resistance, and the like.

The present invention also provides a method for preparing a male sterile plant, wherein the plant male fertility related protein in the plant is made to be expressed at a reduced level, not expressed or inactivated.

As a preferred embodiment of the present invention, the present invention provides a method for preparing a male sterile rice by using the CRISPR-Cas9 technique, which is to knock out or mutate a nucleic acid encoding the plant fertility related protein in rice by using the CRISPR-Cas9 technique.

Specifically, with a target site 1 GCGGTCGGTGGCGGCCATGG (SEQ ID NO: 17) and/or a target site 2 CGCCTCCCTCGCCGTCGCGG (SEQ ID NO: 18) as the target site, the target site 1 or the target site 2 and a nucleotide sequence adjacent to the target site are mutated by using CRISPR-Cas9 technique.

The present invention also provides a method for obtaining an orthologous gene fragment of the GMS2 gene in a plant, and a method for obtaining an amino acid sequence of homologous GMS2 of *Arabidopsis thaliana*, banana, *Oryza glaberrima, Oryza brachyantha*, barley, *sorghum (Sorghum bicolor)*, maize and millet, and uses thereof.

The method for obtaining the orthologous gene fragment of the GMS2 gene in a plant provided by the present invention comprises the following steps: performing a blastx search in a nucleotide database using the DNA fragment of the aforementioned GMS2 gene, and all nucleotide sequences with Identities greater than or equal to 35% and Positives greater than or equal to 50% are gene fragments that are orthologous to the GMS2 gene.

Another object of the present invention is to provide a plant fertility related protein GMS2 mutant, a coding gene thereof, a molecular marker thereof and the uses thereof in hybridization breeding.

According to the present invention, a rice fertility related protein GMS2 mutant is found, which has three amino acids, asparagine, serine and tyrosine, deleted at positions 40 to 42 relative to the wild-type plant male fertility related protein.

GMS2 is located on rice chromosome 4, and its genomic nucleotide sequence in *japonica* rice variety Nipponbare is represented by SEQ ID NO: 1, the CDS sequence is represented by SEQ ID NO: 2, and amino acid sequence is represented by SEQ ID NO: 3. In the indica rice variety 9311, its genomic nucleotide sequence is represented by SEQ ID NO: 4, its CDS sequence is represented by SEQ ID NO: 69, and its amino acid sequence is identical to that of the *japonica* rice variety Nipponbare. The amino acid sequence of the fertility gene in *Arabidopsis lyrata* is represented by SEQ ID NO: 9; the amino acid sequence of the fertility gene in banana (*Musa acuminata*) is represented by SEQ ID NO: 10: the amino acid sequence of the fertility gene in *Oryza glaberrima* is represented by SEQ ID NO: 11: the amino acid sequence of the fertility gene in *Oryza brachyantha* is represented by SEQ ID NO: 12: the amino acid sequence of the fertility gene in barley (*Hordeum vulgare*) is represented by SEQ ID NO: 13: the amino acid sequence of the fertility gene in sorghum (*Sorghum bicolor*) is represented by SEQ ID NO: 14: the amino acid sequence of the fertility gene in maize (*Zea mays*) is represented by SEQ ID NO: 15; and the amino acid sequence of the fertility gene in millet (*Setaria italica*) is represented by SEQ ID NO: 16.

The fertility gene describe above may be isolated from various plants. It should be understood by a person skilled in the art that the fertility gene of the present invention includes a highly homologous functional-equivalent sequence that is highly homologous to the GMS2 gene and has the same fertility regulation function. The highly homologous functional-equivalent sequence includes a DNA sequence capable of hybridizing with the nucleotide sequence of the GMS2 gene disclosed by the present invention under stringent conditions. The "stringent conditions" used in the present invention are well known and include for example hybridization in a hybridization solution containing 400 mM NaCl, 40 mM PIPES (pH6.4) and 1 mM EDTA at 60° C. for 12 to 16 hours, followed by washing with a washing solution containing 0.1% SDS and 0.1×SSC at 65° C. for 15 to 60 minutes.

The functional-equivalent sequence also includes a DNA sequence having at least 85%, 90%, 95%, 96%, 97%, 98%, or 99% sequence similarity with the nucleotide sequence of the GMS2 gene disclosed by the present invention and having fertility regulation function, which may be isolated from any plant. Among them, the percentage of sequence similarity may be obtained by well-known bioinformatics algorithms including Myers and Miller algorithm (Bioinformatics, 4 (1): 1117, 1988), Needleman-Wunsch global alignment method (J Mol Biol, 48 (3): 443-453, 1970), Smith-Waterman local comparison method (J Mol Biol, 147:195-197, 1981), Pearson and Lipman similarity search method (PNAS, 85 (8): 2444-2448, 1988), and Karlin and Altschule algorithm (Altschule et al., J Mol Biol, 215 (3): 403-410, 1990; and PNAS, 90:5873-5877, 1993). This is familiar to a person skilled in the art.

Based on the above findings of the present invention, another aspect of the present invention is to provide a plant male fertility related protein mutant comprising the following amino acid mutations relative to a wild-type plant male fertility related protein: deletion of at least one of the three amino acids N, x and Y in a conserved sequence NxYL;

wherein x is S or N;

the wild-type plant male fertility related protein is the protein described in the following (1) or (2):

(1) a protein having an amino acid sequence represented by SEQ ID NOs: 3, 9, 10, 11, 12, 13, 14, 15 or 16;

(2) a protein with the activity of regulating plant male fertility obtained by substitution and/or deletion and/or addition of one or more amino acid residues in SEQ ID NOs: 3, 9, 10, 11, 12, 13, 14, 15 or 16.

Preferably, the mutant comprises the following amino acid mutations relative to a wild-type plant male fertility related protein: deletion of the three amino acids N, x and Y in a conserved sequence NxYL: wherein x is S or N.

For rice, the mutant comprises the following amino acid mutations relative to a wild-type plant male fertility related protein thereof: deletion of the amino acids at positions 40, 41 and 42, and the wild-type male fertility related protein thereof has the sequence represented by SEQ ID NO: 3, or is a protein with the activity of regulating plant male fertility obtained by substitution and/or deletion and/or addition of one or more amino acid residues in SEQ ID NO: 3

The present invention provides a rice GMS2 protein mutant having an amino acid sequence represented by SEQ ID NO: 8.

The present invention also provides a nucleic acid encoding the plant male fertility related protein mutant.

The nucleic acid of the plant male fertility related protein mutant described by the present invention may be isolated from any plant, including but are not limited to, *Brassica*, maize, wheat, sorghum (*Sorghum bicolor*), *Oryza brachyantha*, *Oryza glaberrima, Brachypodium, Crambe, Brassica alba*, sesame, soybean, *Arabidopsis, Phaseolus* Linn, peanut, *LotuscorniculatusL*, oat, barley, Rye (*Secale cereale L.*), millet, Milo (*Sorghum Moench*), triticale, einkorn (*Triticum monococcum*), Spelt, emmer (*Triticum dicoccum*), flax, Gramma grass, *Tripsacum, Euchlaena mexicana, Festuca ovina L*, Perennial wheatgrass, Coriander, *Vaccinium oxycoccos* Linn, papaya, banana, safflower, oil palm, cantaloupe, apple, cucumber, dendrobium, *gladiolus, chrysanthemum*, plants of the lily family (*Liliaceae*), cotton, sunflower, sugar beet, coffee, ornamental plants and conifer, etc. Preferably, the plants include maize, millet, *Arabidopsis thaliana, Brachypodium distachyon*, soybean, safflower, mustard, wheat, barley, Rye (*Secale cereale L.*), *Oryza brachyantha, Oryza glaberrima*, cotton, and sorghum (*Sorghum bicolor*).

Specifically, taking rice as an example, the nucleic acid encoding the mutant comprises the following nucleotide mutations relative to the nucleic acid encoding the wild-type plant male fertility related protein: deletion of AACAGCTAC bases corresponding to positions 118 to 126 of the coding region of LOC_Os04g48490 gene.

For the rice GMS2 protein mutant, the genome nucleotide sequence of the mutated GMS2 is represented by SEQ ID NO: 6, and the CDS sequence is represented by SEQ ID NO: 7.

The present invention also provides a biological material which is an expression cassette, a vector, a host cell, a transgenic cell line or a transgenic plant containing a nucleic acid encoding the plant male fertility related protein mutant.

Still another aspect of the present invention is to provide any of the following uses of the mutant or the nucleic acid or the biological material:

(1) use in regulating plant male fertility;

(2) use in preparing male sterile plants;

(3) use in plant hybridization breeding;

(4) use in the improvement of plant germplasm resources.

In the above (1), regulating the plant male fertility may reduce or lose the plant male fertility. Specifically, it may be implemented by regulating the development of plant male germ cells and pollen. Among them, the reduction or loss of male fertility in a plant may be implemented by mutating the gene encoding the plant male fertility related protein in a plant so that the protein has reduced expression level or no expression, or by introducing an inhibitory factor of a nucleic acid encoding the plant male fertility related protein into the plant.

In the above (2), the male sterile plant is a recessive genic male sterile line with a homozygous mutation of a nucleic acid encoding the plant male fertility related protein.

In the above (3), hybridization breeding and seed production are performed using a recessive genic male sterile line with a homozygous mutation of a nucleic acid encoding the plant male fertility related protein.

In the above (4), the improvement includes yield improvement, quality improvement, pest and disease resistance, stress resistance, lodging resistance, and the like.

The plants described above are self-pollinated or cross-pollinated plants including, but not limited to, maize, wheat, sorghum (*Sorghum bicolor*) and rice.

Still another aspect of the present invention is to provide a plant, plant tissue, or plant cell with a male sterility trait, in which the protein encoded by a gene of a wild-type plant male fertility related protein in the genome sequence thereof comprises the following amino acid mutations: deletion of at least one of the three amino acids N, x and Y in a conserved sequence NxYL, wherein the wild-type plant male fertility related protein is the same as previously described.

Preferably, the protein encoded by a gene of a wild-type plant male fertility related protein in the genome sequence of the plant, plant tissue or plant cell comprises the following amino acid mutations: deletion of three amino acids N, x and Y in a conserved sequence NxYL.

Preferably, the plant is rice, the plant tissue is rice tissue, and the plant cell is a rice cell.

The present invention provides rice, and a genome or a transcriptome of the rice comprises the following mutations: deletion of AACAGCTAC bases at positions 118 to 126 of a coding region of LOC_Os04g48490 gene, resulting in deletion of asparagine, serine and tyrosine at positions 40, 41 and 42 of a protein encoded by the LOC_Os04g48490 gene: the sequence of the coding region of LOC_Os04g48490 gene is represented by SEQ ID NO: 69, and a sequence of a protein encoded by LOC_Os04g48490 gene is represented by SEQ ID NO: 3.

The present invention also provides a rice tissue, and a genome or a transcriptome of the rice tissue comprises the following mutations: deletion of AACAGCTAC bases at positions 118 to 126 of a coding region of LOC_Os04g48490 gene, resulting in deletion of asparagine, serine and tyrosine at positions 40, 41 and 42 of a protein encoded by LOC_Os04g48490 gene.

The present invention also provides a rice cell, and a genome or a transcriptome of the rice cell comprises the following mutations: deletion of AACAGCTAC base at positions 118 to 126 of a coding region of LOC_Os04g48490 gene, resulting in deletion of asparagine, serine and tyrosine at positions 40, 41 and 42 of a protein encoded by LOC_Os04g48490 gene.

The present invention further provides a rice, rice tissue or rice cell in which the sequence of LOC_Os04g48490 gene in the genome sequence is mutated to a sequence represented by SEQ ID NO: 6, and thus the CDS of the LOC_Os04g48490 gene is mutated to a sequence represented by SEQ ID NO: 7, and the encoded protein is mutated to a sequence represented by SEQ ID NO: 8.

The present invention provides a rice mutant material gms2, and gms2 exhibits male sterility, in which the sequence of LOC_Os04g48490 (GMS2) gene in the genome sequence is mutated to a sequence represented by SEQ ID NO: 6, the CDS of LOC_Os04g48490 gene is mutated to a sequence represented by SEQ ID NO: 7, and the amino acid sequence of the encoded protein is mutated to a sequence represented by SEQ ID NO: 8: LOC_Os04g48490 gene in the genome sequence is represented by SEQ ID NO: 4.

Specifically, the AACAGCTAC bases at positions 118 to 126 in a coding region of (sequence represented by SEQ ID NO: 69) LOC_Os04g48490 (GMS2) gene in the genome sequence of the rice mutant material gms2 was deleted, resulting in the deletion of asparagine, serine and tyrosine at positions 40, 41 and 42 in the protein encoded by LOC_Os04g48490 gene.

The above deletion of asparagine, serine and tyrosine at positions 40, 41 and 42 of GMS2 causes the loss of function of GMS2 protein and further leads to male sterility in rice.

A person skilled in the art should understand that the nucleotide sequence represented by SEQ ID NO: 6 may be introduced into a receiver plant by methods of hybridization, backcross or transgenosis, thereby obtaining a new male sterile mutant material.

Still another aspect of the present invention is to provide a molecular marker for detecting the mutant or the mutant material, and the molecular marker is obtained by amplification with primers having nucleotide sequences represented by SEQ ID NOs. 19-20.

The present invention provides specific primers for amplifying the molecular marker, and the nucleotide sequences thereof are represented by SEQ ID NOs: 19-20.

The present invention provides a detection reagent or kit containing primers having nucleotide sequences represented by SEQ ID NOs: 19-20.

The present invention also provides any one of the following uses of the molecular marker or the detection reagent or kit:

(1) use in detecting the plant male fertility related protein mutant or the mutant material; and (2) use in screening or cultivating a male sterile rice mutant.

Specifically, when the primers represented by SEQ ID NOs: 19-20 are selected to amplify the rice genomic DNA, if only one band of 140 bp is amplified, the rice expresses the plant male fertility related protein mutant, has a homozygous genotype of deletion of AACAGCTAC bases at positions 118 to 126 of the coding region of LOC_Os04g48490 gene, and exhibits a male sterility trait: if only one band of 149 bp is amplified, the rice does not express the plant male fertility related protein mutant, does not have the genotype of deletion of AACAGCTAC bases at positions 118 to 126 of the coding region of LOC_Os04g48490 gene, and exhibits a male fertility trait: if two bands of 140 bp and 149 bp are amplified at the same time, the rice expresses the plant male fertility related protein mutant, has a heterozygous genotype of deletion of AACAGCTAC bases at positions 118 to 126 of the coding region of LOC_Os04g48490 gene and exhibits a male fertility trait.

Still another aspect of the present invention is to provide a method for preparing a male sterile plant comprising: making mutation in a wild-type plant male fertility related protein, the mutation comprises the following amino acid mutation: deletion of at least one of the three amino acids N, x and Y in a conserved sequence NxYL: the wild-type plant male fertility related protein is the same as described above.

Preferably, the plant is rice, and the method comprises: making mutation in a genome or a transcriptome of the rice, the mutation comprise the following mutation: deletion of AACAGCTAC bases at positions 118 to 126 of a coding region of LOC_Os04g48490 gene, resulting in deletion of asparagine, serine and tyrosine at positions 40, 41 and 42 of a protein encoded by the LOC_Os04g48490 gene: a sequence of the coding region of the LOC_Os04g48490 gene is represented by SEQ ID NO: 69, and a sequence of the protein encoded by the LOC_Os04g48490 gene is represented by SEQ ID NO: 3.

More preferably, the method comprises: making rice express a male fertility related protein mutant having a sequence represented by SEQ ID NO: 8 and not express a wild-type plant male fertility related protein represented by SEQ ID NO: 3.

The above mutation may be realized by methods of gene edition, hybridization, backcross, self-fertilization or vegetative propagation.

Compared with the prior art, the present invention has the following beneficial effects: the rice pollen development regulatory gene GMS2 provided by the present invention directly participates in the regulation of pollen development, and after the gene is knocked out or its expression is inhibited, the pollen is completely sterile, resulting in male sterility of a plant. In the present invention, gene editing is performed on the GMS2 gene by using CRISPR-Cas9 gene editing technology, and the rice male sterile mutant with a mutated GMS2 gene is obtained. Compared with the existing three-line and two-line sterile lines, the rice sterile mutant caused by the GMS2 mutation has stable sterile trait and is not affected by environmental conditions. With the GMS2 gene and the mutant thereof, a new genic male sterile line can be cultivated by methods such as transgenosis and the like, and a method for restoring the fertility of the male sterile line is provided, which lays a foundation for culturing and breeding the rice genic male sterile line and playing an important role in the utilization of the heterosis of crops and the production of sterile hybrid seed production. The rice male fertility regulatory protein GMS2 mutant provided by the present invention may make the rice pollen completely sterile, resulting in rice male sterility. The genic sterile mutant of the present invention may be used for culturing a new genic sterile line, and provides a simple, rapid and effective method for culturing the rice genic sterile line. Compared with the existing three-line and two-line sterile lines, the rice sterile mutant caused by the GMS2 mutant has the advantages of stable sterile trait, high utilization rate of germplasm resources and the like, and may be used for recurrent selective breeding that requires a large amount of hybridization, and has a great application value in the field of hybrid rice breeding and seed production.

BRIEF DESCRIPTION OF THE DRAWINGS

FIG. 8A is a map of GMS2 gene map-based cloning in Example 4 of the present invention.

FIG. 8B is a schematic diagram of the mutation sites of the gms2 mutant in Example 4 of the present invention.

FIG. 9 shows differences in nucleotide sequences of GMS2 gene in materials 9311 (48490-9311), Minghui 63 (48490-MH63), Nipponbare (48490-Nip) and gms2 mutant (48490-3148) in Example 4 of the present invention. The differences are highlighted with a grey background. The position of the last nucleotide of each line in the whole gene sequence is marked at the end of the line. The start codon ATG and the stop codon TGA are marked with a square, respectively.

FIG. 10 shows differences in amino acid sequences of the GMS2-encoded protein in 9311 (48490-9311) and the gms2 mutant (48490-3148) in Example 4 of the present invention. The differences are highlighted with a light grey background. The position of the last amino acid residue in each line in the whole protein sequence is marked at the end of the line.

FIG. 11 shows the genotype identification of the offsprings of the GMS2 heterozygous plants in Example 4 of the present invention. The upper band is 149 bp in size and the lower band is 140 bp in size. The arrows points to samples from male sterility.

FIG. 12 shows the expression levels of GMS2 in different tissues and different development stages of young panicles of rice in Example 5 of the present invention. Flowers 1 to 9 represent the stage of spikelet primordium differentiation to the pollen maturation stage during the development of young panicles.

FIG. 26 is a sequence alignment diagram of the protein encoded by the GMS2 gene of rice in Example 9 of the present invention with homologous proteins in genomes of other species including protein AT3G60900.1 of *Arabidopsis lyrata*, protein GSMUA_Achr11P03090_001 of banana (*Musa acuminata*), protein ORGLA04G0194100.1 of *Oryza glaberrima*, protein OB04G29380.1 of *Oryza brachyantha*, protein MLOC_7985.1 of barley (*Hordeum vulgare*), protein Sb06g026030.1 of *sorghum* (*Sorghum bicolor*), protein GRMZM2G003752_P01 of maize (*Zea mays*), and protein Si010135m of millet (*Setaria italica*). The conserved sequence NxYL is marked with a square.

SPECIFIC MODES FOR CARRYING OUT THE EMBODIMENTS

Figure 1:
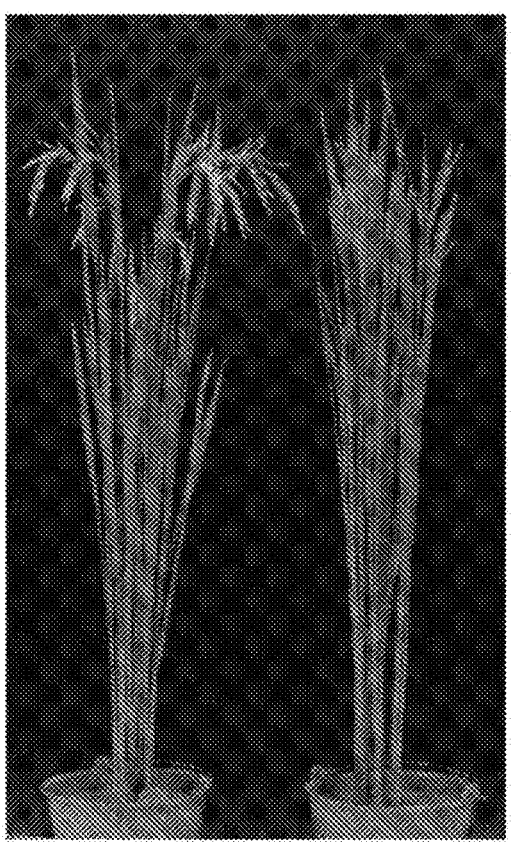
FIG. 1 shows the morphologies of plants of the wild type (left) and the gms2 mutant (right) at the filling stage in Example 2 of the present invention.

The following examples facilitate a better understanding of the present invention but do not limit the scope of application of the present invention. All technical and scientific terms in the following examples have the same meanings as commonly understood by a person skilled in the art unless otherwise specified. The techniques used or referred to in the present invention are standard techniques recognized by a person skilled in the art unless indicated to the contrary. The test materials, unless otherwise specified, are the test materials commonly used in the field of the present invention. The test reagents used in the examples below, unless otherwise specified, are commercially available from the conventional biochemical reagent stores.

The male sterility described in the present invention specifically refers to the abnormal development of male reproductive organs of plants (unable to produce normal stamens, anthers or normal male gametophytes) and the loss of fertility due to functional changes in plant nuclear genes, which is commonly referred to as Genic male sterility rather than Cytoplasmic male sterility. Both abnormality and restoration of fertility in the male reproductive organs are controlled by genes within the nucleus.

Therefore, the present invention also includes utilizing the sequences described in the sequence listings to regulate and control the male gamete fertility of the plant, i.e., utilizing the gene sequences provided by the present invention to affect the functions of the same or homologous genes in other plants at the levels of genome, and/or transcriptome, and/or proteome so as to achieve the purpose of controlling the fertility of the male reproductive organ. For example, it includes but is not limited to the following methods: affecting or altering the functions of plant genes by mutating natural sequences and thereby resulting in inhibition of gene expression or loss of protein function, by transferring antisense sequences of said genes into plants or introducing hairpin structures, or by combining said genes with other sequences (DNA or RNA) to generate novel functionally active DNA or RNA chains. Or any of the other technical methods known to a person skilled in the art that can be used to affect male fertility in plants.

The present invention includes a rice GMS2 gene, a dominant allele of which has a key effect on male fertility of a plant, and a recessive allele with loss-of-function can lead to male sterility. The gene is located on rice chromosome 4, and the specific location of the gene is shown in FIGS. 8A and 8B.

The sequence of the gene and its homologous sequence can be obtained from various plants including, but not limited to, *Selaginella moellendorffii*, *Populus trichocarpa*, *Brassica rapa*, *Arabidopsis lyrata*, *Arabidopsis thaliana*, soybean (*Glycine max*), potato (*Solanum tuberosum*), grape (*Vitis vinifera*), *Musa acuminata*, millet (*Setaria italica*), sorghum (*Sorghum bicolor*), maize (*Zea mays*), *Brachypodium distachyon*, barley (*Hordeum vulgare*), *Oryza brachyantha*, *Oryza glaberrima*, *Oryza sativa* Indica Group, *Oryza sativa Japonica* Group, *Physcomitrella patens* and the like. The obtaining methods include, but are not limited to, retrieving from the genome sequence database, and/or cDNA sequence database, and/or protein sequence database of other plants using rice GMS2 gene sequence through blastx or blastn, or using rice GMS2 amino acid sequence through blastp: obtaining directly from genomic DNA or cDNA or RNA of other plants by using a PCR method with primers designed using the DNA or cDNA or RNA sequence of the rice GMS2 gene as a reference sequence; and isolating DNA or cDNA or RNA fragments containing the homologous gene sequences from genomic libraries by nucleic acid hybridization method using probes designed based on the sequence of GMS2 gene in rice.

The homologous sequence of GMS2 gene refers to the gene sequence of plant with Identity greater than or equal to 35% and Positive greater than or equal to 50% after blastp comparative analysis with the amino acid sequence of SEQ ID NO: 3. When performing blastp, all parameters follow the default settings shown in blast.ncbi.nlm.nih.gov/.

The following provides a more detailed description by way of illustration and description, but is not intended to limit the scope of the present invention.

Example 1: Screening of Rice Male Sterile Mutant Gms2

In June 2013, 10 kg of 93-11 seeds were irradiated with cobalt 60 to obtain the $M_0$ generation. The irradiated seeds were planted in an experimental field in Lingao County, Hainan Province, and after maturity, plants were harvested individually to obtain seeds, and a total of about 6,500 materials of $M_1$ generation were obtained. In the spring of 2014, 3,617 $M_1$ generation materials with a higher seed amount were selected and planted into lines, with 50 individual plants per line. Various types of mutants such as plant type, panicle type, fertility and yield were screened at tillering stage, booting stage, heading stage, flowering stage and filling stage, respectively, and the seeds of the selected mutants were collected and stored.

Among them, a sterile mutant named gms2 was found in line No. 3148.

Example 2: Phenotypic Analysis of Rice Male Sterile Mutant Gms2

Figure 2:
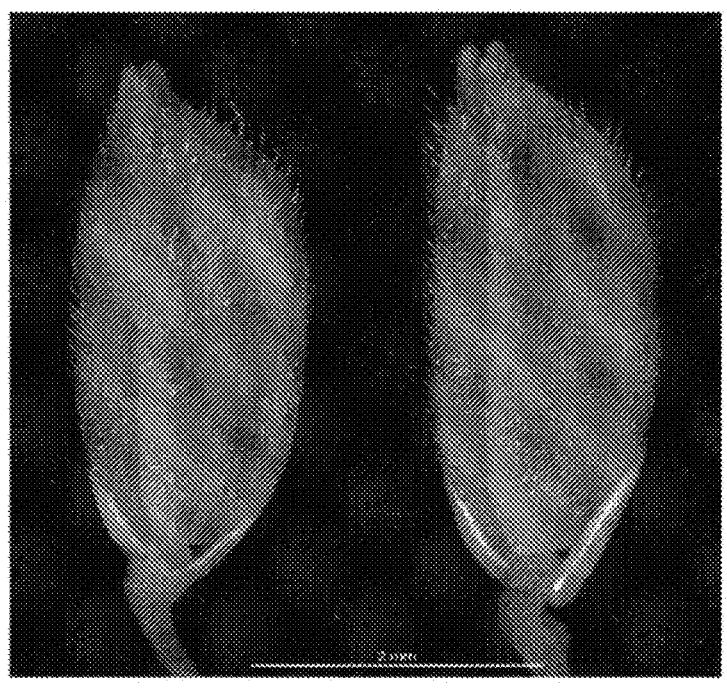
FIG. 2 shows the morphologies of spikelets of the wild type (left) and the gms2 mutant (right) in Example 2 of the present invention.
Figure 3:
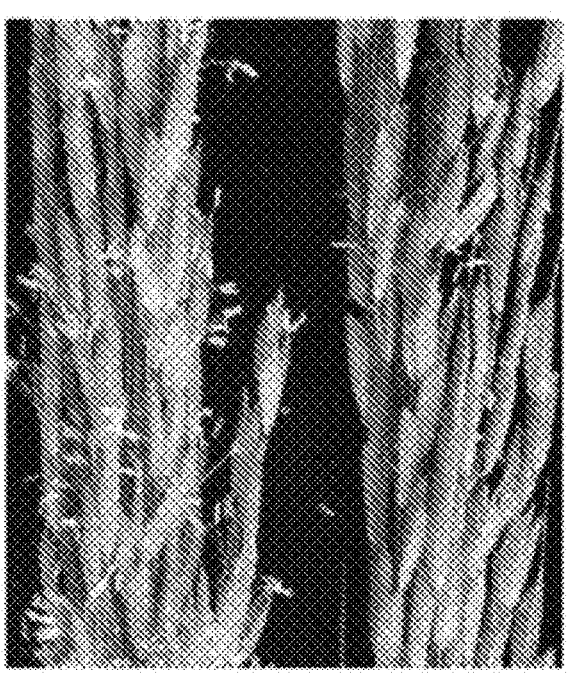
FIG. 3 shows the morphologies of flowers of the wild type (left) and the gms2 mutant (right) in Example 2 of the present invention.
Figure 4:
FIG. 4 shows the morphologies of florets of the wild type (left) and the gms2 mutant (right) after dissection in Example 2 of the present invention.
Figure 5:
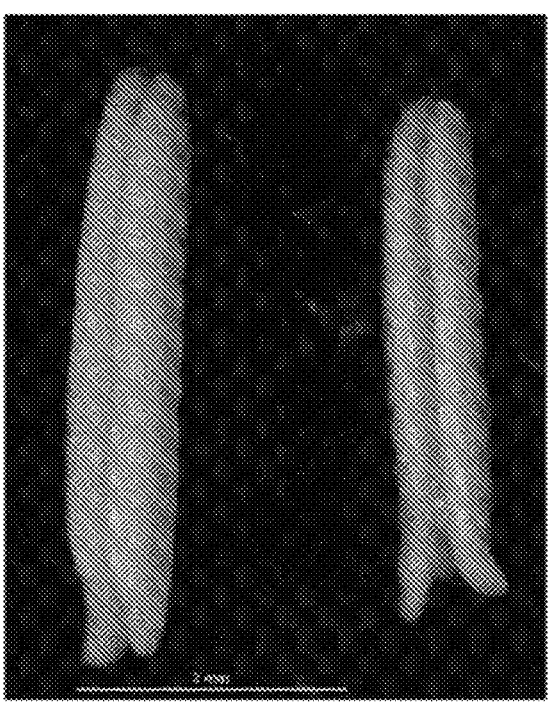
FIG. 5 shows the morphologies of anthers of the wild type (left) and the gms2 mutant (right) in Example 2 of the present invention.
Figure 6:
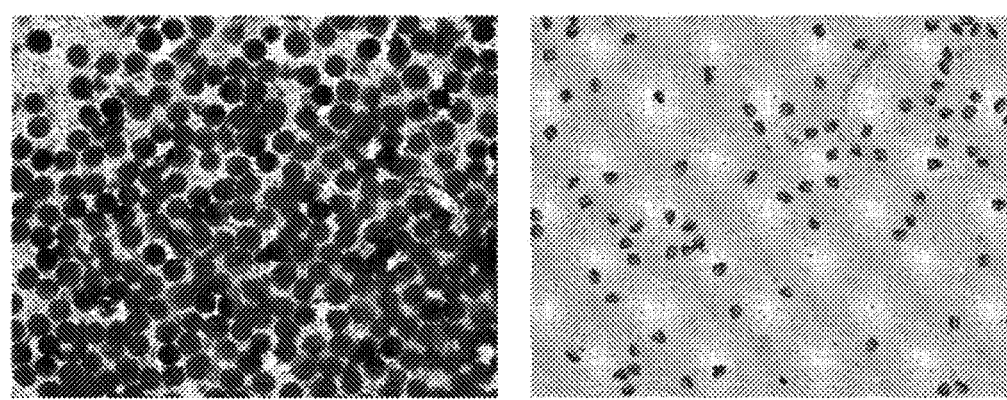
FIG. 6 shows the iodine staining results of pollen of the wild type (left) and the gms2 mutants (right) in Example 2 of the present invention.

Compared with the wild type, the plants and spikelets of the gms2 mutant were morphologically normal (FIG. 1), and the flowering stage was slightly late (FIG. 2). There is no significant difference in palea and lemma size, floret opening size and opening time from those of the wild type (FIG. 3). The floret morphology of the mutant was observed under the stereoscopic microscope, and it was found that the ovary, style and stigma were slightly larger than those of the wild type (FIG. 4), but the anthers were thinner, smaller and lighter in color as compared with the wild type (FIG. 5). The pollen was stained with iodine-potassium iodide solution (0.6% KI, 0.3% $I_2$, w/w), and as shown in FIG. 6, the wild-type pollen grains were large and round and stained blue-black, while the mutant pollen grains were shrunken and could not be stained. The wild-type plants in the same family were normally fruit-bearing after bagging selfing, while the gms2 mutants were not. However, using rice variety 93-11 as a male parent to pollinate gms2 mutant, the gms2 mutant can bear fruit. This indicates that the mutant is a male sterile mutant.

Example 3: Genetic Analysis of Rice Male Sterile Mutant Gms2

In M5 generation, 80 plants of segregating population of gms2 were planted, of which 64 were normal in fertility and 16 were sterile, and the segregation ratio of fertile and sterile plants was 3:1 ($\chi^2=0.57$, P>0.05). By backcrossing gms2 with 93-11, all the F1 generation plants were fertile. In the F2 generation, 70 plants of segregating population of gms2 were planted, of which 57 were normal in fertility and 13 were sterile, and the segregation ratio of fertile to sterile plants was 3:1 ($\chi^2=0.85$, P>0.05). The above results indicated that the male sterility of gms2 is controlled by a single recessive gene.

Example 4: Cloning of Rice Male Sterility Gene GMS2

Figure 7:
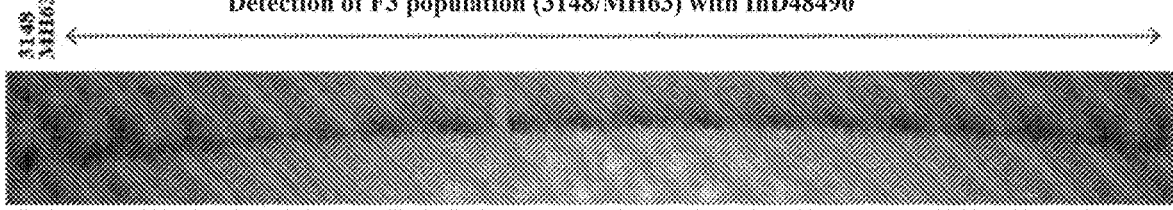
FIG. 7 shows the genotypes of the sterile individual plants in the mapping population identified using the InD48490 marker in Example 4 of the present invention. The upper band is 149 bp in size and the lower band is 140 bp in size. The DNA templates of the two leftmost lanes are the gms2 mutant and Minghui 63 (MH63), respectively, and the latter lanes are the sterile individual plants in the mapping population.

The GMS2 gene was mapped by the map-based cloning method. An F2 population containing 66 mutant plants was constructed by crossing Minghui 63 as a male parent with the gms2 mutant. Using this population, GMS2 was mapped to 6861.252 Kb between SSR markers RM17332 and RM280 on chromosome 4, and was closely linked to SSR marker RM303 and Indel marker 4826. There were 8, 1, 1 and 32 recombinant individual plants between GMS2 gene and the above four markers, respectively. The linkage markers were used to select the gms2 heterozygous plants in the F2 population to develop an F3 population containing 1937 mutant individual plants. There were 10, 7 and 8 recombinant individual plants between RM303, 4826 and S10, and GMS2 genes in the F3 population, respectively. By analyzing and comparing the sequences of 93-11 and Minghui 63 genomes between RM303 and S10, five new Single Nucleotide Polymorphism (SNP) markers S4b, S3b, S2, S1 and S8 were developed and experimentally confirmed. In the F3 population, there were 6, 6, 1, 4 and 8 recombinant individual plants for the above markers, respectively (FIG. 7).

Using 77 kb upstream and downstream of S2 as the candidate segment, a total of 11 annotation genes were found in this segment, among which LOC_Os04g48490 was predicted to encode a fasciclin-like arabinogalactan protein, and presumed to be the GMS2 gene. In Nipponbare, the nucleotide sequence of the LOC_Os04g48490 in genome was 1582 bp long (denoted as 48490-Nip, the sequence was represented by SEQ ID NO: 1) and the nucleotide sequence of CDS was 1296 bp long (the sequence was represented by SEQ ID NO: 2), one exon (FIGS. 8A and 8B) was contained, and a protein with a length of 432 amino acid residues (the sequence was represented by SEQ ID NO: 3) was encoded. The sequences of the marker primer pairs used for mapping the GMS2 gene are shown in Table 1 (SEQ ID NOs. 39-68).

TABLE 1

Sequences of the marker primer
pairs used for mapping the GMS2 gene

| Name of the markers | Forward primers | Reverse primers |
|---|---|---|
| RM17332 | CGGTACATCACGGTATCAAATCG (SEQ ID NO: 39) | TAAATGCTGGAGCGATGCTAAC C (SEQ ID NO: 40) |
| RM280 | GTGCTCTCCATGTCGGATTATGC (SEQ ID NO: 41) | CAAGGCAACAAGATTGGTTAGT GG (SEQ ID NO: 42) |
| RM17351 | ATAAAGGAGGAGGGCCTCAGATGG (SEQ ID NO: 43) | CACGGTTTGGAGGTTGGAAGC (SEQ ID NO: 44) |
| RM17352 | GCTTGGCATCTGCTTCTGTTGTTGG (SEQ ID NO: 45) | CTCGCTGCTGATCGAGGTGTCG (SEQ ID NO: 46) |
| RM303 | ATCGATGTAGGTAGAGGGACACC (SEQ ID NO: 47) | CAGATCTAGTCGACATGGTTGG (SEQ ID NO: 48) |
| 4826 | ACACCATCTCTCTTCTTTTTCTAT (SEQ ID NO: 49) | ATATGGGTAGGTTTGGATATTC G (SEQ ID NO: 50) |
| S4b | GTGTGTGTGAGTAAAATCCTAGTGC A (SEQ ID NO: 51) AAAAAGTGTGTGTGAGTAAAATCCT AGAGCC (SEQ ID NO: 53) | ATTTGTACTCCTATGTTTAGAA TAGC (SEQ ID NO: 52) |
| S3b | ACAAATATATAGCAAAATCGGTGAC C (SEQ ID NO: 54) AAAAAACAAATATATAGCAAAATCG GTTACG (SEQ ID NO: 56) | GTGGTTTTGTGGATGTTTTGTA ACT (SEQ ID NO: 55) |
| S2 | AAGTATTTGTAATGCACTATGTAAA GGT (SEQ ID NO: 57) AAAAAAAGTATTTGTAATGCACTAT GTAATGGC (SEQ ID NO: 59) | TTAAGAGCACACACTTCCAATA ATATGT (SEQ ID NO: 58) |
| S1 | CTGGGCGCGGTGCGGCGGGCGAGGC (SEQ ID NO: 60) AAAAACTGGGCGCGGTGCGGCGGGC GTGGT (SEQ ID NO: 62) | CCGCCTCAGCGCCACCGCCAAG CTGA (SEQ ID NO: 61) |
| S8 | AAGTTGTGTTTAGCACTATGTTATT ACG (SEQ ID NO: 63) AAAAAAAGTTGTGTTTAGCACTATG TTATGACA (SEQ ID NO: 65) | TTTAGCATAATAACTACTATTC ATCATT (SEQ ID NO: 64) |
| S10 | GCAGGAGACACTTGGTGCCGCCTCT C (SEQ ID NO: 66) AAAAAGCAGGAGACACTTGGTGCCG CCACTT (SEQ ID NO: 68) | GCAGATTATTTTCGGTGGGTCC CGTCTC (SEQ ID NO: 67) |

According to the sequence of 48490-Nip, primers were designed and used to amplify and sequence the alleles of LOC_Os04g48490 gene in 93-11, Minghui 63 and the gms2 mutant, the primer sequences are shown in Table 2. All PCR amplifications were performed using KOD FX DNA Polymerase (TOYOBO CO., LTD. Life Science Department, Osaka, Japan) and PCR amplification was performed on Thermo Scientific Arktik Thermo cycler according to the reaction system and conditions described in the product description. The PCR products were sent to Nanjing GenScript Biotechnology Co., Ltd. for sequencing. The sequencing results were assembled with DNAman 6.0. The LOC_Os04g48490 genes in 93-11, Minghui 63, and the gms2 mutant were recorded as 48490-9311 (the sequence was represented by SEQ ID NO: 4), 48490-MH63 (the sequence was represented by SEQ ID NO: 5) and 48490-3148 (the sequence was represented by SEQ ID NO: 6), respectively.

TABLE 2

| Sequences of a primer pair for amplification of LOC_Os04g48490 | | |
| --- | --- | --- |
| Name of the markers | Forward primers | Reverse primers |
| LOC_Os04g48490_1 | AAACAGAAAGCCCCA ATG (SEQ ID NO: 21) | TGCCGCAGTACGCGC CCAAG (SEQ ID NO: 22) |
| LOC_Os04g48490_2 | TTGTCCATGCCGGTG TCCAT (SEQ ID NO: 23) | GGTCACGGCACAAAC TCA (SEQ ID NO: 24) |

Multiple sequence alignments of 48490-9311, 48490-3148, 48490-MH63 and 48490-Nip were performed, and the results are shown in FIG. 9. Compared with 48490-9311, 48490-3148 has only one deletion of AACAGCTAC starting at base 118 behind ATG (FIGS. 8B and 9). Amino acid sequence analysis revealed that this mutation would lead to the deletion of asparagine, serine, and tyrosine residues at positions 40 to 42 in the protein encoded by the LOC_Os04g48490 gene (FIG. 10). Compared with 48490-MH63 and 48490-Nip, 48490-3148 has the same difference at base 118 behind ATG as described above (FIG. 9). This indicates that the deletion mutation of AACAGCTAC starting at base 118 behind ATG is responsible for the male sterility of the gms2 mutant. In addition, the sequences of 48490-9311 and 48490-MH63 were identical, and compared with 48490-Ni, there is a SNP from A to Cat position 8, a SNP from C to G at position 109, a SNP at position 1288 from T to C, and an insertion of G base at position 1515 (FIG. 9). Two nucleotide differences fall in 5'UTR and 3'UTR respectively, and the other two nucleotide differences fall in the exons, but they do not affect the coded protein. This indicates that the LOC_Os04g48490 gene is highly conserved in rice, and the nucleotide sequence thereof differs in only 4 bases even between subspecies of indica and japonica, while there is no difference in protein sequences. The CDS nucleotide sequence of LOC_Os04g48490 in 93-11 is represented by SEQ ID NO: 69, and the coded protein sequence is represented by SEQ ID NO: 3. The CDS nucleotide sequence and the amino acid sequence of LOC_Os04g48490 in the gms2 mutant are represented by SEQ ID NO: 7 and SEQ ID NO: 8, respectively.

Based on the sequencing results of the mutation site of LOC_Os04g48490 gene, specific primers IND48490_F: GCTCCGGCTGTTGATCT (SEQ ID NO: 19) and IND48490_R: GCCTGCTCTTCCTCCTG (SEQ ID NO: 20) were designed on both sides of the mutation site. When InD48490_F and InD48490_R were paired to amplify the wild type LOC_Os04g48490 gene, a 149 bp band would be generated, while a 140 bp band would be generated when the mutant LOC_Os04g48490 gene was amplified. Genotyping was performed on the M6 segregating population of 41 gms2 plants using InD48490_F and InD48490_R primer pairs. As shown in FIG. 11, the wild type amplified either 2 bands of 149 bp and 140 bp or 1 band of 149 bp, while all of the sterile mutants could only amplify 1 band of 140 bp.

This indicates that the mutant genotype co-segregates with the sterile phenotype, and LOC_Os04g48490 is the GMS2 gene.

Example 5: Expression Analysis of GMS2 Gene

Total RNA was extracted from tissues at every period from 93-11 and reverse transcribed into cDNA. The expression level of the GMS2 gene was detected using primers InD48490_F: GCTCCGGCTGTTGATCT (SEQ ID NO: 19) and InD48490_R: GCCTGCTCTTCCTCCTG (SEQ ID NO: 20). The expression level of the internal reference gene GAPDH was detected using primers GAPDH-RTF: GAATGGCTTTCCGTGTT (SEQ ID NO: 25) and GAPDH-RTR: CAAGGTCCTCCTCAACG (SEQ ID NO: 26). Real-time quantitative PCR was used for expression analysis. As shown in FIG. 12, the expression level of GMS2 gene was significantly lower in roots and stems than in other tissues, and significantly higher in seeds than in other tissues. In stem nodes, leaves, sheaths and spikes, the expression level of GMS2 gene was moderate, but not the same. In Flowers 1 (flower length of 1 mm), 2 (flower length of 2 mm), 3 (flower length of 3 mm), 4 (flower length of 4 mm), 5 (flower length of 5 mm), 6 (flower length of 5.5 mm), 7 (flower length of 6 mm), 8 (flower length of 7 mm) and 9 (flower length of 8 mm), that is, in spikes from the stage of spikelet primordium differentiation to the pollen maturation stage, the expression amount of GMS2 decreased first, then increased and finally decreased again.

Example 6: Acquisition and Phenotypic Analysis of GMS2 Gene Knockout Lines

Figure 13:
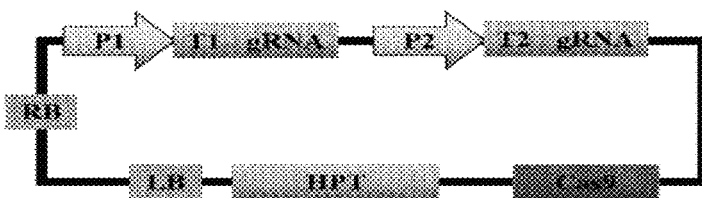
FIG. 13 is a schematic diagram of a pC9M-GMS2 vector in Example 6 of the present invention. T1 represents the target site 1, and T2 represents the target site 2.

Targeted knockout of GMS2 gene was performed using CRISPR-Cas9 system. In order to improve the knockout efficiency, two target sites were selected for simultaneous knockout. Target site 1 was located on the negative strand of the exon, and the sequence is GCGGTCGGTGGCGGC-CATGG (SEQ ID NO: 17, located at positions 45 to 64 of SEQ ID NO: 1), and Target site 2 was located on the exon and the sequence is CGCCTCCCTCGCCGTCGCGG (SEQ ID NO: 18, located at positions 85 to 104 of the sequence of SEQ ID NO: 1). Target site 1 and Target site 2 were ligated into the vector pC9M to obtain the vector pC9M-GMS2 (FIG. 13) according to the method of Ma et al. (Ma X, et al. A Robust CRISPR-Cas9 System for Convenient, High-Efficiency Multiplex Genome Editing in Monocot and Dicot Plants. Mol Plant, 2015, 8:1274-84). E. coli with pC9M-GMS2 is designated E. coli-pC9M-GMS2. The pC9M-GMS2 was transformed into Agrobacterium strain EHA 105 by electroporation, and the resulting strain was designated Ab-pC9M-GMS2.

The callus of the japonica rice Zhonghua 11 (ZH11) was infected with the recombinant Agrobacterium Ab-pC9M-GMS2, and 25 regenerated transgenic lines were obtained through hygromycin resistance screening, differentiation and rooting. After acclimation and transplantation, 22 surviving plants were obtained, and the total DNA of the leaves of the plants was extracted, and primers SP1: CCCGA-CATAGATGCAATAACTTC (SEQ ID NO: 29) and SP2: GCGCGGTGTCATCTATGTTACT (SEQ ID NO: 30) were used for positive detection, all of the plants were positive plants. The genomic DNA was amplified with primers of target 1-F: AAACCCACGCCCAGAAA (SEQ ID NO: 31) and target 1-R: GCCAGGAGGAAGAGCAG (SEQ ID NO: 32) on both sides of Target site 1 and primers of target 2-F: GCCTGCTCTTCCTCCTG (SEQ ID NO: 33) and 2-R:

GTGCTCCGGCTGTTGAT (SEQ ID NO: 34) on both sides of Target site 2. The amplified products were sequenced and subjected to genome alignment. The results showed that gene editing was occurred in 14 plants of TO, wherein homozygous mutation was occurred in one plant, and 8 seedlings of TO-generation were not edited.

Figure 14A:
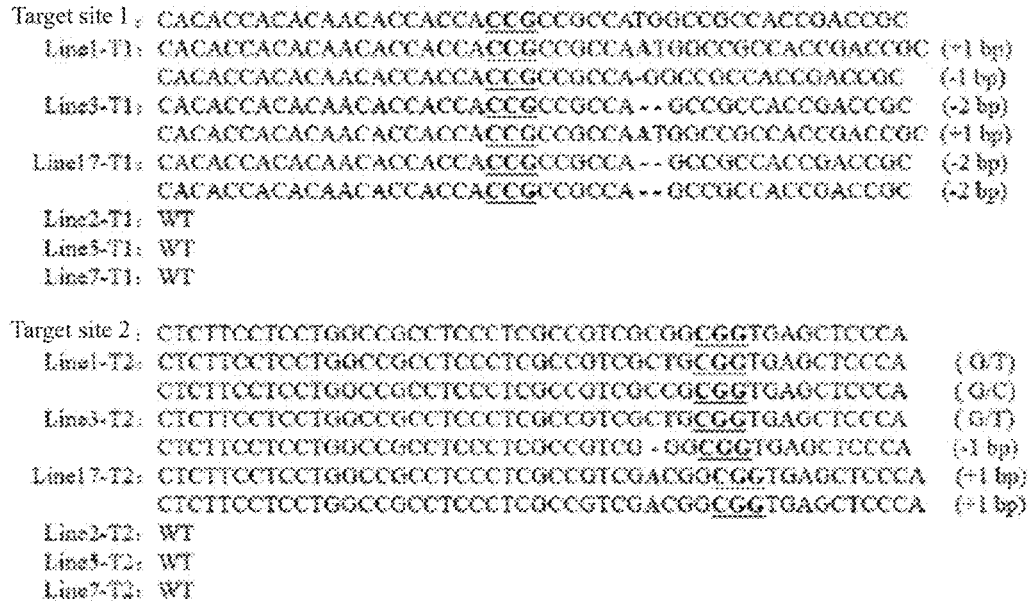
FIG. 14A shows the sequence analysis for the target sites of some transgenic positive plants after the GMS2 gene is knocked out by using the CRISPR/Cas9 system in Example 6 of the present invention.
Figure 14B:
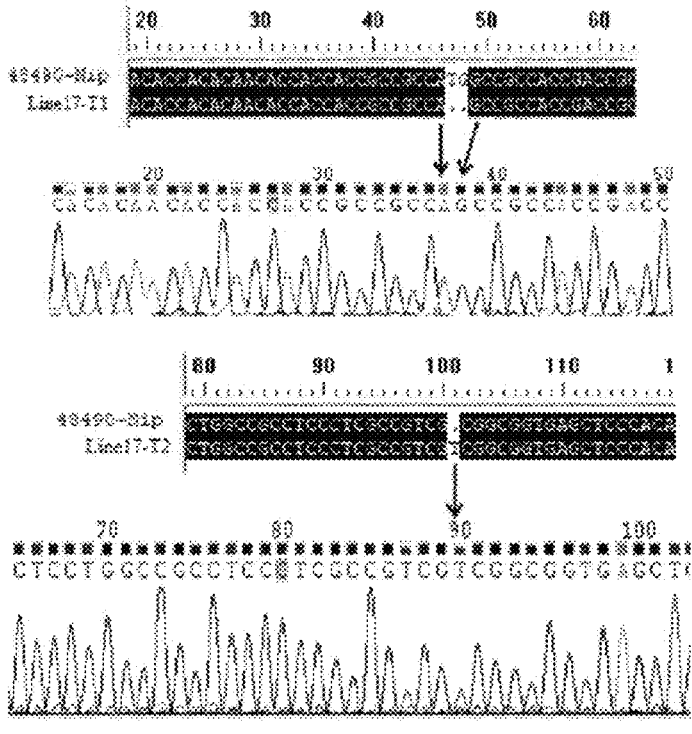
FIG. 14B are sequencing peak maps at the target site 1 and the target site 2 of the transgenic plant(s) PC9M-GMS2-Line17 in Example 6 of the present invention. Among them, in the sequencing peak map at the target site 1, the arrow points to a deletion site; and in the sequencing peak map at the target site 2, the arrow points to the insertion site.

Homozygous mutations were occurred at both Target site 1 and Target site 2 of the genomic DNA of plant PC9M-GMS2-Line17, in which deletion of TG bases (SEQ ID NO: 27) occurs at Target site 1, and insertion of T base (SEQ ID NO: 28) occurs at Target site 2 (FIG. 14B). Biallelic mutation was occurred at Target site 1 of the genomic DNA of PC9M-GMS2-Line1, in which insertion of A base occurs at allele 1, and deletion of T base occurs at allele 2: biallelic mutation was also occurred at Target site 2 of the genomic DNA of PC9M-GMS2-Line1, with a G/T base SNP at allele 1, and a G/C base SNP at allele 2. Biallelic mutation was occurred at Target site 1 of the genomic DNA of PC9M-GMS2-Line3, with deletion of TG bases at allele 1 and insertion of A base at allele 2: biallelic mutation was also occurred at Target site 2 of the genomic DNA of PC9M-GMS2-Line3, with a G/T base SNP at allele 1 and deletion of C base at allele 2. However, the genotypes of transgenic-negative individual plants PC9M-GMS2-Line2, PC9M-GMS2-Line5, and PC9M-GMS2-Line7 were not altered (FIG. 14A).

Figure 15:
FIG. 15 shows the morphologies of the whole plants of the wild type (left) and knockout plant PC9M-GMS2-Line17 (right) of GM2 in Example 6 of the present invention.
Figure 16:
FIG. 16 shows the morphologies of glumes of the wild type (left) and knockout plant PC9M-GMS2-Line17 (right) of GM2 in Example 6 of the present invention.
Figure 17:
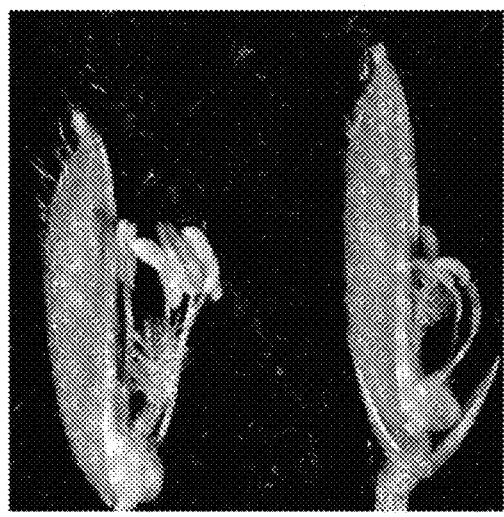
FIG. 17 shows the morphologies of anthers of the wild type (left) and knockout plant PC9M-GMS2-Line17 (right) of GMS2 in Example 6 of the present invention.
Figure 18:
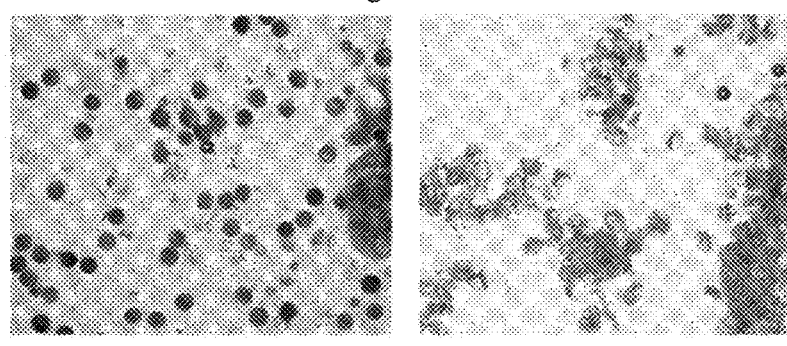
FIG. 18 shows the iodine staining results of pollen of the wild type (left) and knockout plant PC9M-GMS2-Line17 (right) of GMS2 in Example 6 of the present invention.

Phenotypic analysis was performed on the above positive plants after flowering. Compared with wild-type ZH11, GMS2 knockout plant PC9M-GMS2-Line17 showed no significant difference in leaf and spikelet morphology (FIGS. 15 and 16). However, the anthers of the GMS2 knockout plants were significantly thinner and smaller (FIG. 17). The results of iodine staining of pollen showed that the pollen of wild type ZH11 was large and round and could be stained, while the pollen of the GMS2 knockout plants was small and shrunken and could not be stained (FIG. 18). Other GMS2 biallelic mutant plants also exhibited the trait of male sterility.

Figure 19:
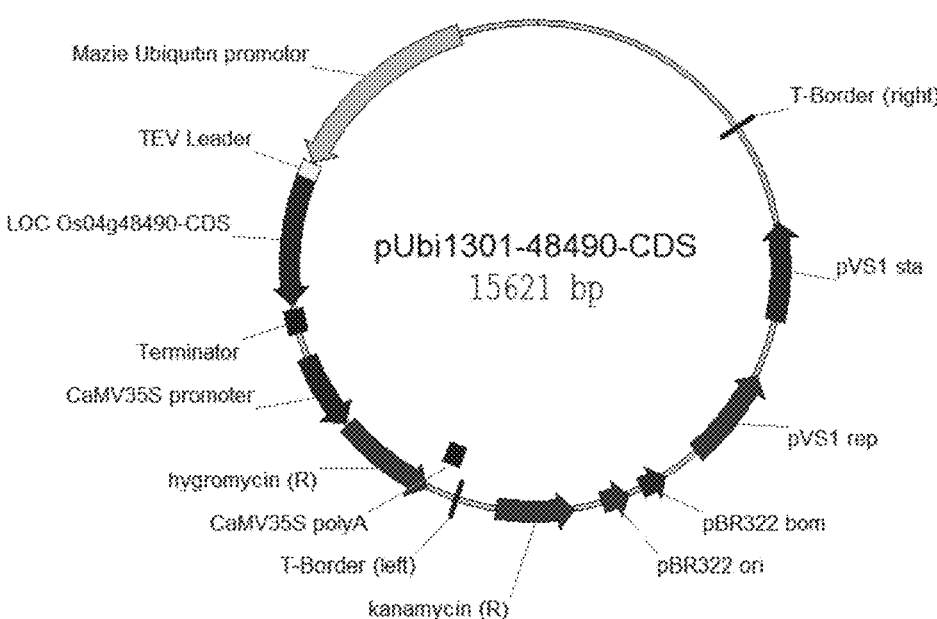
FIG. 19 is a schematic diagram of a pUbi1301-48490-CDS vector in Example 7 of the present invention.

Example 7: Acquisition and Phenotypic Analysis of a GMS2 Gene Overexpressing Lines Using the RNA reverse transcription product of 9311 as a template, a DNA fragment with a GMS2 complete coding nucleotide sequence (SEQ ID NO: 2) was obtained by amplification using primers 3148OX-F: CggggtaccATGGCCGCCACCGAC: (SEQ ID NO: 35) and 3148OX-R: CGCggatccTCACAAGAACGACGC (SEQ ID NO: 36). The fragment was double-digested with Kpn I and BamH I and then ligated into pBLU5 to obtain plasmid pUbi1301-48490-CDS (FIG. 19). *E. coli* with pUbi1301-48490-CDS is designated *E. coli*-pUbi1301-48490-CDS. The pUbi1301-48490-CDS was transformed into *Agrobacterium* strain EHA105 by electroporation, and the resulting strain was designated Ab-pUbi1301-48490-CDS.

Figure 20:
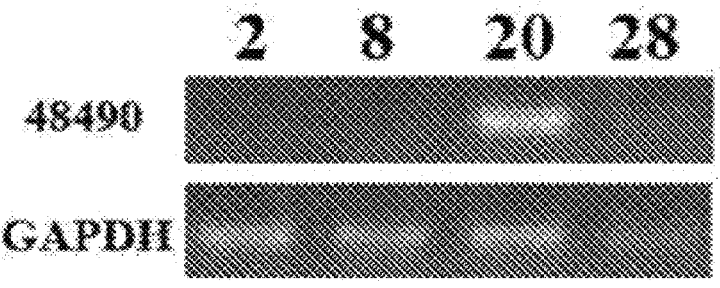
FIG. 20 shows the RT-PCR analysis of the expression level of GMS2 in the overexpressed plants in Example 7 of the present invention. The histogram is the result obtained by quantifying the band brightness in the RT-PCR gel image and dividing the brightness values of 48490 by the brightness values of the corresponding GAPDH.
Figure 20:
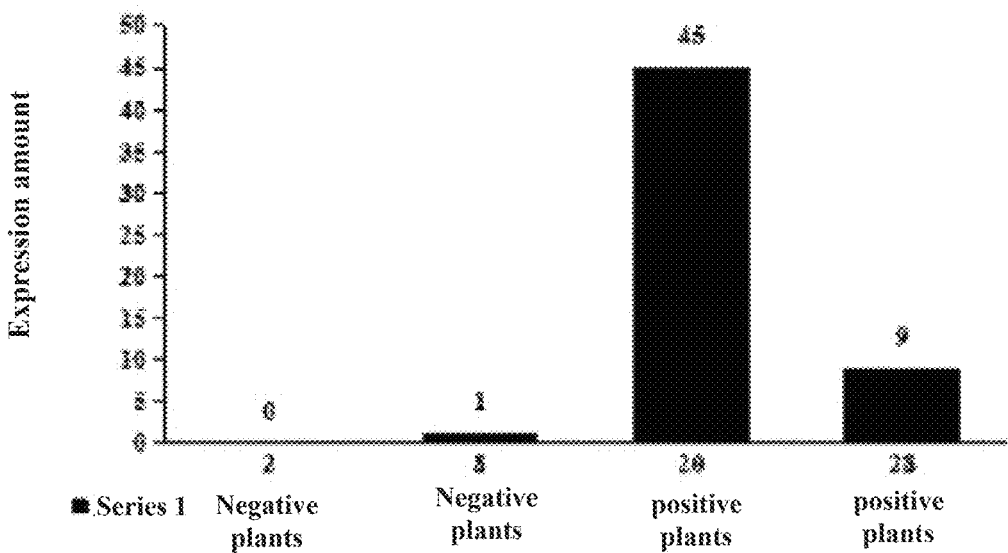

The callus of the *japonica* rice Zhonghua 11 was infected with the recombinant *Agrobacterium* Ab-pUbi1301-48490-CDS, and 6 transgenic positive plants were obtained through hygromycin resistance screening, differentiation and rooting. The expression amounts of GMS2 in transgenic positive plants were analyzed using the real-time quantitative PCR method with the primers InD 48490-F: GCTCCGGCTGTT-GATCT (SEQ ID NO: 19) and InD 48490-R: GCCTGCTCTTCCTCCTG (SEQ ID NO: 20), GAPDH-RTF: GAATGGCTTTCCGTGTT (SEQ ID NO: 25) and GAPDH-RTR: CAAGGTCCTCCTCAACG (SEQ ID NO: 26) in Example 5. As shown in FIG. 20, compared with transgenic negative individual plants 2 and 8, the expression amounts of GMS2 in overexpression plants 20 and 28 were increased by 9-fold and 45-fold, respectively, however, there was no significant phenotype that was co-segregated with the expression amount in the overexpressed plants, which indicates that the overexpression of GMS2 gene had no significant effect on rice phenotype.

Figure 21:
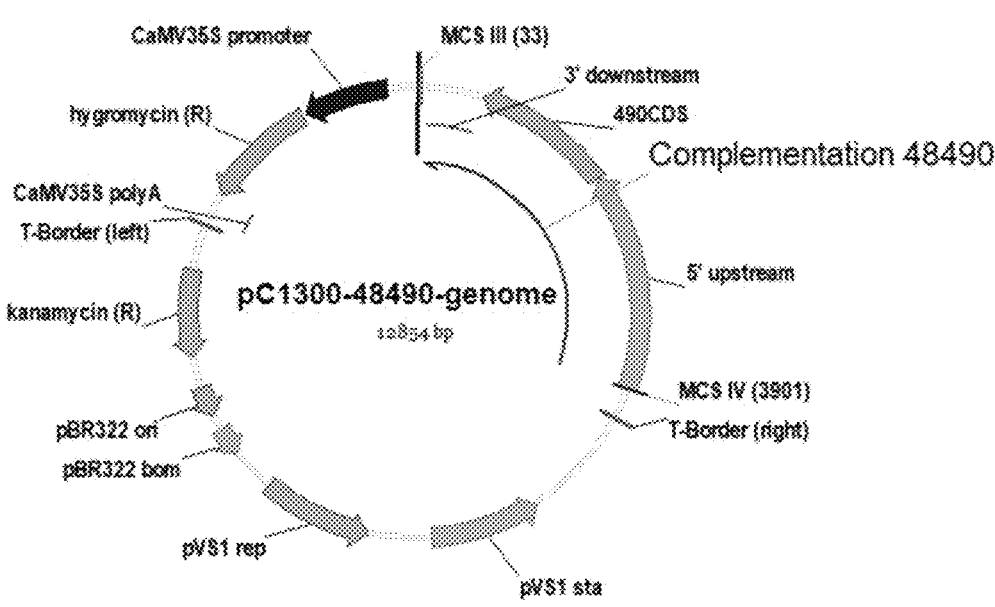
FIG. 21 is a schematic diagram of a pC1300-48490-genome vector according to Example 8 of the present invention.
Figure 22:
FIG. 22 shows the morphologies of plants of the wild type (left) and the gms2 mutant complementary plant (right) in Example 8 of the present invention.
Figure 23:
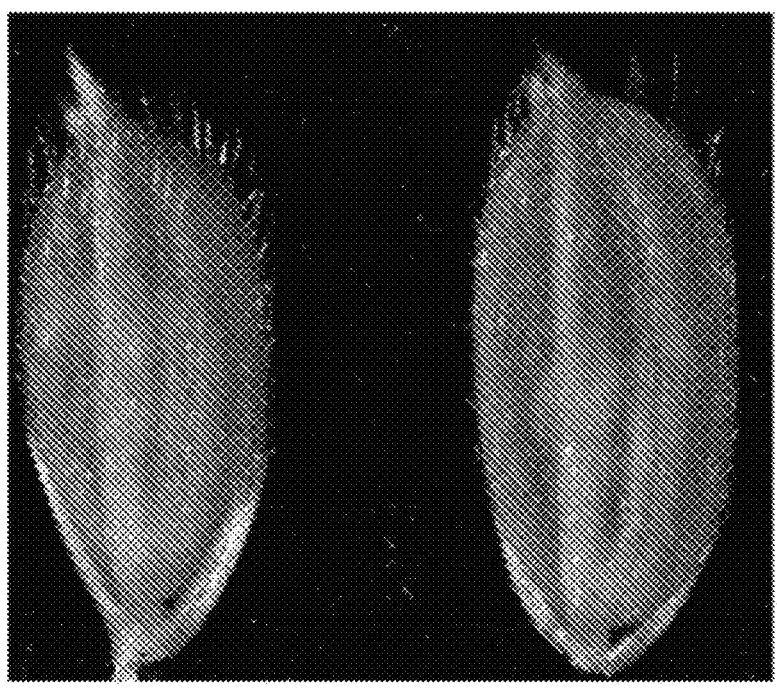
FIG. 23 shows the morphologies of glumes of the wild type (left) and the gms2 mutant complementary plant (right) in Example 8 of the present invention.
Figure 24:
FIG. 24 shows the morphologies of anthers of the wild type (left) and the gms2 mutant complementary plant in Example 8 of the present invention.
Figure 25:
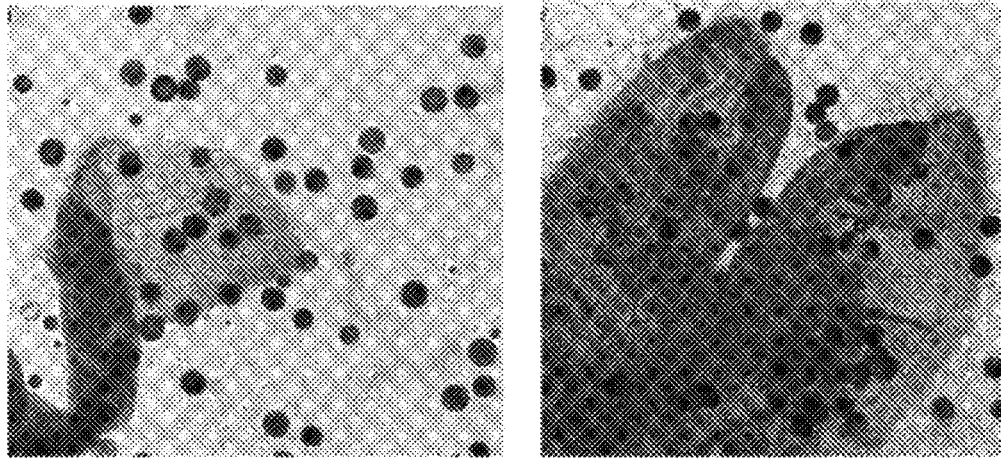
FIG. 25 shows the iodine staining results of pollen of the wild type (left) and the gms2 mutant complementary plant in Example 8 of the present invention.

Example 8: Acquisition and Phenotypic Analysis of a Transgenic Complementary Line of Gms2 Mutant Using the genomic DNA of 9311 as a template, a full-length fragment of the gene with 2 kb upstream of the starting codon ATG of GMS2 and 515 bp downstream of the stopping codon TGA of GMS2 was obtained by amplification with primers 3148HB-F: CgcgtttcgaaatttTGATTTCTT-CATCGCACT (SEQ ID NO: 37) and 3148HB-R: GtcgcgatcgcatgcACAACATGGTGCAACAGTG (SEQ ID NO: 38). The fragment was ligated into the pC1300 after double digestion with Kpn I and BamH I to obtain the plasmid pC1300-48490-genome (FIG. 21). The *E. coli* with pC1300-48490-genome is designated *E. coli*-pC1300-48490-genome. The PC1300-48490-genome was transformed into *Agrobacterium* strain EHA105 by electroporation, and the resulting strain was designated Ab-pC1300-48490-genome. The callus of gms2 mutant was infected with recombinant *Agrobacterium* Ab-pC1300-48490-genome, and 4 transgenic positive plants were obtained through resistance screening, differentiation and rooting, and the fertility of the four plants was restored to normal (FIGS. 22, 23, 24 and 25). This further proved that the GMS2 gene regulates and controls pollen development, and the mutation of this gene would lead to pollen abortion.

Figure 26:
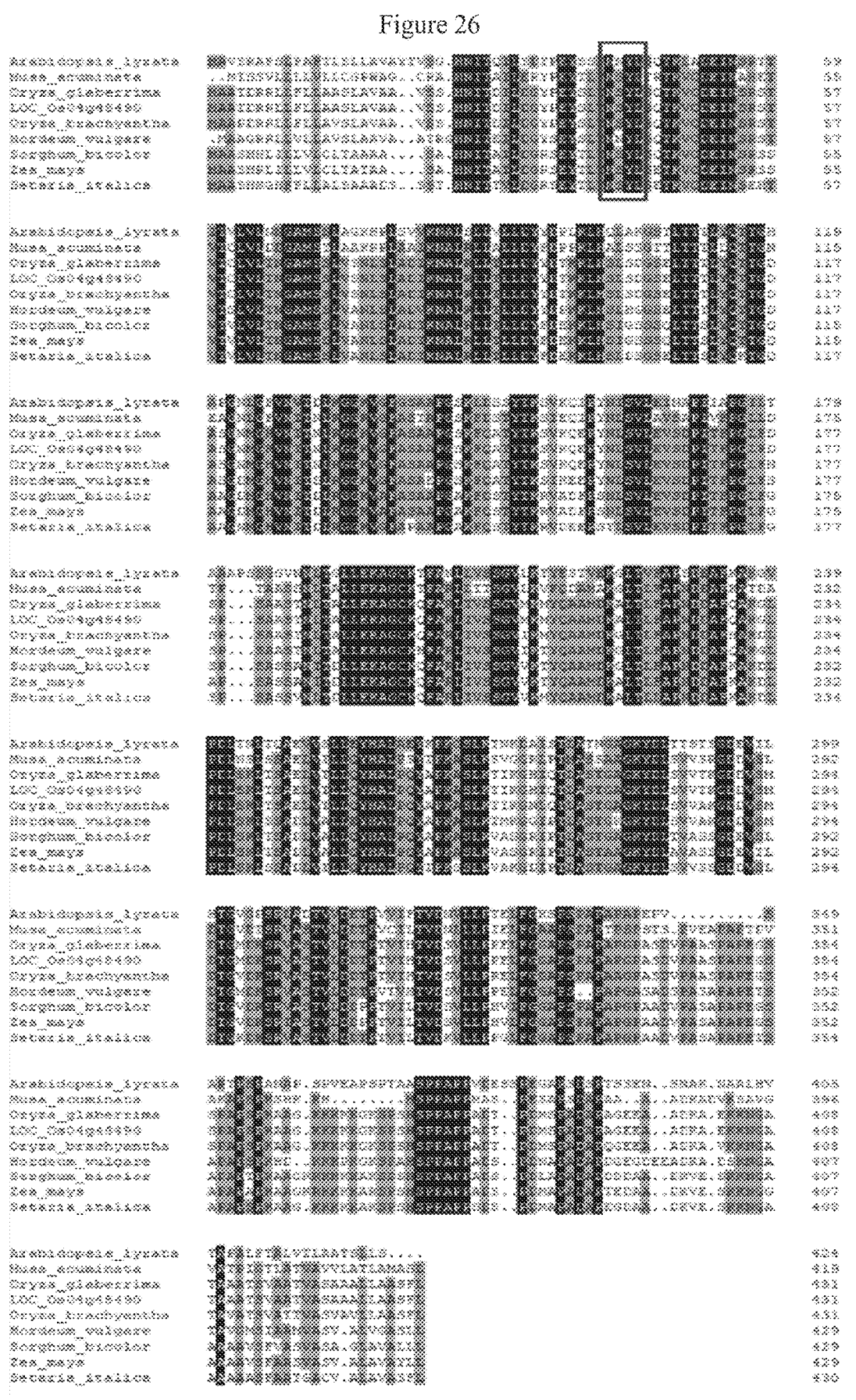
Figure 27:
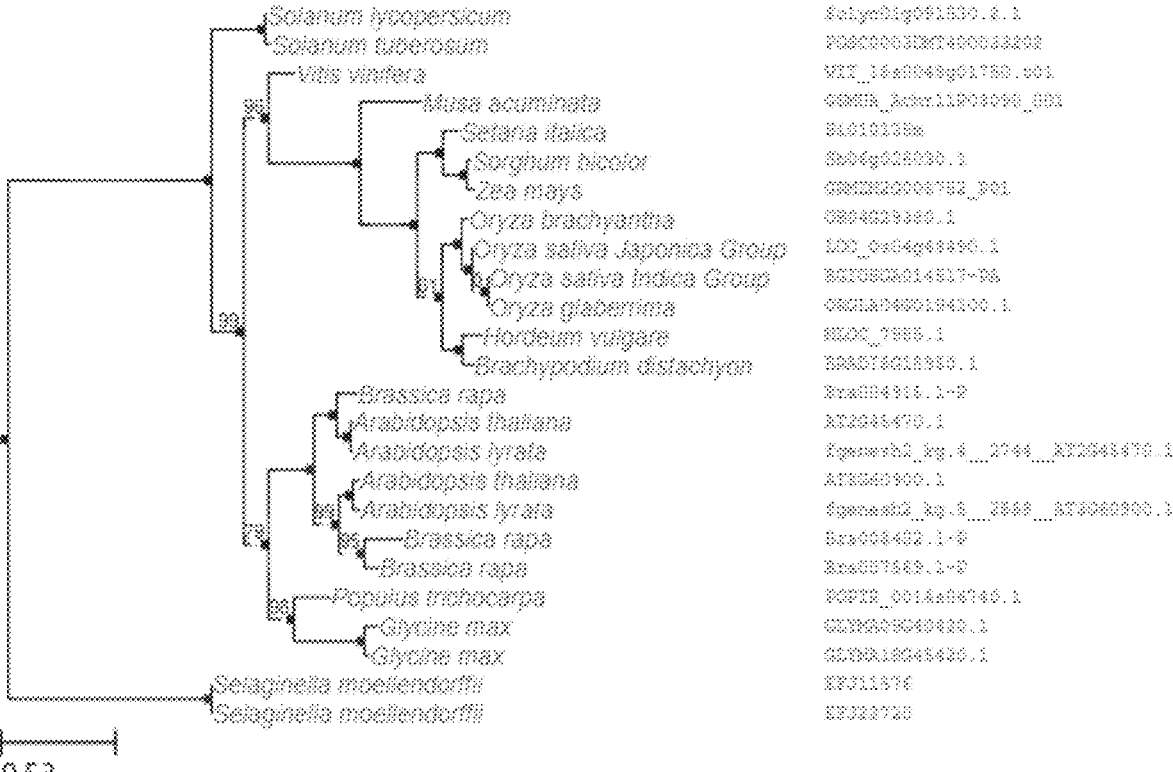
FIG. 27 shows the phylogenetic tree analysis of the protein encoded by the GMS2 gene of rice in Example 9 of the present invention.

Example 9: Sequence Alignment and Phylogenetic Tree Analysis of GMS2-Encoded Protein and its Homologous Proteins Performing homology search on the amino acid sequence of the protein encoded by the rice GMS2 gene in Genbank database of NCBI by using a blastp tool, the predicted homologous proteins in the genomes of *Arabidopsis lyrata*, banana (*Musa acuminata*), *Oryza glaberrima, Oryza brachyantha*, barley (*Hordeum vulgare*), sorghum (*Sorghum bicolor*), maize (*Zea mays*) and millet (*Setaria italica*) were obtained, these protein sequences were aligned and analyzed, and the results showed that the homologous proteins from different plants all had very similar conserved sequences and high homology with each other (FIGS. 26 and 27), indicating that the protein has a conservative biological function and plays a very important role during the development of male organs of plant flowers.

The amino acid sequence of the fertility gene in *Arabidopsis lyrata* is represented by SEQ ID NO: 9; the amino acid sequence of the fertility gene in banana (*Musa acuminata*) is represented by SEQ ID NO: 10; the amino acid sequence of the fertility gene in *Oryza glaberrima* is represented by SEQ ID NO: 11: the amino acid sequence of the fertility gene in *Oryza brachyantha* is represented by SEQ ID NO: 12: the amino acid sequence of the fertility gene in barley (*Hordeum vulgare*) is represented by SEQ ID NO: 13: the amino acid sequence of the fertility gene in sorghum (*Sorghum bicolor*) is represented by SEQ ID NO: 14: the amino acid sequence of the fertility gene in maize (*Zea mays*) is represented by SEQ ID NO: 15; and the amino acid sequence of the fertility gene in millet (*Setaria italica*) is represented by SEQ ID NO: 16.

Example 10: Breeding of Recessive Genic Male Sterile Line with GMS2 Gene

Hybridizing, backcrossing and selfing were performed on the gms2 mutant with a fertility-normal receptor such as rice variety H28B, and the gms2 gene and genetic background were selected with molecular markers in the process, and the recessive genic male sterile line with the homozygous GMS2 mutation gene under the background of H28B was finally obtained. The specific implementation steps were as follows:

1. a receptor parent such as H28B was used as a male parent to hybridize with a gms2 mutant to obtain $F_1$.
2. F1 was used as a female parent to backcross with a receptor parent such as H28B to obtain $BC_1F_1$.
3. $BC_1F_1$ was planted, and the gms2 genotypes were detected using the primers InD48490_F: GCTCCGGCTGTTGATCT (SEQ ID NO: 19) and InD48490_R: GCCTGCTCTTCCTCCTG (SEQ ID NO: 20). The plant with heterozygous gms2 genotype (the plant that may amplify 149 bp and 140 bp bands simultaneously) was selected.
4. the individual plants selected in step 3 was subjected to genetic background identification using a set (e.g., 100, or 200 and the like) of evenly distributed molecular markers (which may be but not limited to SSR, SNP, INDEL, EST, RFLP, AFLP, RAPD, SCAR, and other types of molecular markers) with genotype polymorphism between the genomes of gms2 mutant and the recurrent parent, and the plants with high genotype similarity to the recurrent parent (e.g., greater than 88% similarity, or 2% selection rate and the like) were selected.
5. the plant selected in step 4 was used to backcross with a receptor parent such as H28B to obtain $BC_2F_1$.
6. $BC_2F_1$ was planted, and steps 3 and 4 were repeated to select the plants with heterozygous gms2 genotype and high genetic background recovery rate (e.g., greater than 98%, or a selection rate of 2%, etc.) and the selfed seeds $BC_2F_2$ were harvested.
7. $BC_2F_2$ was planted, and steps 3 and 4 were repeated to select the plants with heterozygous gms2 genotype and the highest homozygosity rate of the genetic background, and the selfed seeds $BC_2F_3$ were harvested. The gms2 homozygous plant segregated from the off-springs of $BC_2F_3$ was the gms2 recessive genic male sterile line, and $BC_2F_3$ was used to preserve the germplasm resources of the gms2 recessive genic male sterile line.

Although the present invention has been described in detail by general description and specific embodiments above, some modifications or improvements can be made on the basis of the present invention, which is obvious to a person skilled in the art. Therefore, all such modifications or improvements made without departing from the spirit of the present invention are within the scope claimed to be protected by the present invention.

INDUSTRIAL APPLICABILITY

The present invention provides a rice male fertility regulatory gene, the use thereof and a method for regulating rice fertility using CRISPR-Cas9, and a mutant of the rice male fertility regulatory gene and a molecular marker and the use thereof. The present invention provides a rice gene GMS2 with the function of regulating male germ cell development in rice and pollen fertility, the nucleotide sequence of which is represented by SEQ ID NO: 1, the CDS sequence is represented by SEQ ID NO: 2 and the amino acid sequence is represented by SEQ ID NO: 3. The rice male fertility regulatory protein GMS2 mutant provided by the present invention can make the rice pollen completely sterile, resulting in rice male sterility, the genome nucleotide sequence of the GMS2 mutant is represented by SEQ ID NO: 6, the CDS sequence is represented by SEQ ID NO: 7 and the amino acid sequence is represented by SEQ ID NO: 8. The genic sterile mutant of the present invention can be used for culturing a new genic sterile line, which provides a simple, rapid and effective method for the cultivation of the rice genic sterile line. The genic sterile rice material of the present invention can be used for replacing artificial emasculation during rice hybridization and saving labor, can be particularly used for recurrent selection breeding which needs a large amount of hybridization and plays an important role in expanding the germplasm basis of rice. The rice gene GMS2 and the mutant thereof provided by the present invention can be used for sterility breeding and production of rice hybrid seeds, and have a great application and economic value.

---

What is claimed is:

1. A method for preparing a male sterile plant, wherein the plant is rice, comprising: mutating a male fertility related protein of a wild-type plant, wherein the male fertility related protein of the wild-type plant has an amino acid sequence represented by SEQ ID NO: 3.

2. The method for preparing a male sterile plant according to claim 1, wherein, the method comprises: mutating the genome or transcriptome of rice, the mutation is a mutation of a nucleic acid having the nucleotide sequence represented by SEQ ID NO: 1, 2, 4 or 69, and the mutation is deletion, insertion or substitution of one or more nucleotides, or a mutation generated by the transformation of an antisense gene, co-suppression or introduction of a hairpin structure; the mutation results in reduced expression, no expression or inactivation of the protein having the amino acid sequence represented by SEQ ID NO: 3.

3. The method for preparing a male sterile plant according to claim 1, wherein, the method comprises: making rice express a male fertility related protein mutant having a sequence represented by SEQ ID NO: 8 and not express a wild-type plant male fertility related protein represented by SEQ ID NO: 3.

4. A method for restoring the male sterility of rice caused by GMS2 gene mutation, wherein the method comprises: introducing a nucleic acid encoding a functional protein into the male sterility of rice by genetic transformation to restore wild-type traits, wherein the functional protein has the amino acid sequence represented by SEQ ID NO: 3.

* * * * *

SEQUENCE LISTING

<160> NUMBER OF SEQ ID NOS: 69

<210> SEQ ID NO 1
<211> LENGTH: 1582
<212> TYPE: DNA
<213> ORGANISM: Artificial Sequence
<220> FEATURE:
<223> OTHER INFORMATION: Laboratory synthesis

<400> SEQUENCE: 1

```
ctccccaccg tgtcacacca caccacacaa caccaccacc gccgccatgg ccgccaccga      60
ccgccgcctg ctcttcctcc tggccgcctc cctcgccgtc gcggcggtga gctcccacaa     120
catcacggac atcctcgacg gctacccgga gtactcgctg tacaacagct acctctccca     180
gaccaaggtg tgcgacgaga tcaacagccg gagcacggtc acctgcctcg tgctcaccaa     240
cggcgccatg tcctccctcg tctccaacct ctccctcgcc gacatcaaga acgcgctccg     300
```

```
cctcctcacc ctcctcgact actacgacac caagaagctg cactccctca gcgacggctc       360
cgagctcacc accacgctgt accagaccac cggcgacgcc tccggtaaca tgggccacgt       420
caacatcacc aacctgcgcg gcggcaaggt tgggttcgcc tccgccgcgc ccggctccaa       480
gttccaggcc acctacacca agtccgtcaa gcaggagccg tacaacctct ccgttcttga       540
ggtctccgac cccatcacct tccccggcct cttcgactcc ccgtcggccg cgtcgaccaa       600
cctcaccgcg cttcttgaga aggccgggtg caagcagttc gcgcggctca tcgtgtcgtc       660
cggggtgatg aagatgtacc aggcggccat ggacaaggcg ctgacgctgt tcgcgcccaa       720
cgacgacgcg ttccaggcca agggcctgcc ggatctgagc aagctgacca gcgccgagct       780
ggtgacgctt ctgcagtacc acgccttgcc gcagtacgcg cccaaggcgt cgctcaagac       840
catcaagggc cacatccaga ccctggcctc caccggagcg ggtaagtacg acctctccgt       900
cgtcactaag ggcgacgacg tgtccatgga caccggcatg gacaagtccc gcgtcgcgtc       960
caccgtgctg gacgacaccc cgacggttat ccacacggtg gacagcgtgc tgctgccgcc      1020
agagctcttc ggtggcgcac cttcccccgc gccggcgccc ggaccggcaa gcgatgtgcc      1080
agccgcttct cccgcgccag aaggctcctc gccggcgccc tccccaagg cggcgggcaa       1140 gaagaaaaag aagggcaagt cgccttccca ttccccaccc gcgcctccgg ccgacacgcc      1200
tgacatgtcg cccgccgacg cgcccgcggg agaagaggct gcagacaaag ccgagaagaa      1260
gaacggcgcc accgcggcgg ccacgagcgt tgcggccact gtggcctccg ccgccgctct      1320
gctcgccgcg tcgttcttgt gagcgtcagg tgttcgacgt tgagctctcg ttgttccccc      1380
ctgggcatgc atggtgtgat gcagtccggt gttcgcttct gagctcgtgg gctccatgga      1440
taatctcatc ctgaagttgt gttcttctct tcctggttgg tagtactcgg tagttagata      1500
ggatttgaat gattggatcc tcaggtggag aacggtgatt gtgatgccta ttttgttaga      1560
gctcggaacc atgttttgtt tt                                              1582
```

```
<210> SEQ ID NO 2
<211> LENGTH: 1296
<212> TYPE: DNA
<213> ORGANISM: Artificial Sequence
<220> FEATURE:
<223> OTHER INFORMATION: Laboratory synthesis

<400> SEQUENCE: 2
```

```
atggccgcca ccgaccgccg cctgctcttc ctcctggccg cctccctcgc cgtcgcggcg        60
gtgagctccc acaacatcac ggacatcctc gacggctacc cggagtactc gctgtacaac       120
agctacctct cccagaccaa ggtgtgcgac gagatcaaca gccggagcac ggtcacctgc       180
ctcgtgctca ccaacggcgc catgtcctcc ctcgtctcca acctctccct cgccgacatc       240
aagaacgcgc tccgcctcct caccctcctc gactactacg acaccaagaa gctgcactcc       300
ctcagcgacg gctccgagct caccaccacg ctgtaccaga ccaccggcga cgcctccggt       360
aacatgggcc acgtcaacat caccaacctg cgcggcggca aggttgggtt cgcctccgcc       420
gcgcccggct ccaagttcca ggccacctac accaagtccg tcaagcagga gccgtacaac       480
ctctccgttc ttgaggtctc cgaccccatc accttcccocg cctcttcga ctccccgtcg       540 gccgcgtcga ccaacctcac cgcgcttctt gagaaggccg ggtgcaagca gttcgcgcgg       600
ctcatcgtgt cgtccggggt gatgaagatg taccaggcgg ccatggacaa ggcgctgacg       660
ctgttcgcgc ccaacgacga cgcgttccag gccaagggcc tgccggatct gagcaagctg       720
```

```
accagcgccg agctggtgac gcttctgcag taccacgcct tgccgcagta cgcgcccaag      780
gcgtcgctca agaccatcaa gggccacatc cagaccctgg cctccaccgg agcgggtaag      840
tacgacctct ccgtcgtcac taagggcgac gacgtgtcca tggacaccgg catggacaag      900
tcccgcgtcg cgtccaccgt gctggacgac accccgacgg ttatccacac ggtggacagc      960
gtgctgctgc cgccagagct cttcggtggc gcaccttccc ccgcgccggc gcccggaccg     1020
gcaagcgatg tgccagccgc ttctcccgcg ccagaaggct cctcgccggc gccctccccc     1080
aaggcggcgg gcaagaagaa aaagaagggc aagtcgcctt cccattcccc acccgcgcct     1140
ccggccgaca cgcctgacat gtcgcccgcc gacgcgcccg cgggagaaga ggctgcagac     1200
aaagccgaga agaagaacgg cgccaccgcg gcggccacga gcgttgcggc cactgtggcc     1260
tccgccgccg ctctgctcgc cgcgtcgttc ttgtga                              1296
```

```
<210> SEQ ID NO 3
<211> LENGTH: 431
<212> TYPE: PRT
<213> ORGANISM: Artificial Sequence
<220> FEATURE:
<223> OTHER INFORMATION: Laboratory synthesis

<400> SEQUENCE: 3

Met Ala Ala Thr Asp Arg Arg Leu Leu Phe Leu Leu Ala Ala Ser Leu
1               5                   10                  15

Ala Val Ala Ala Val Ser Ser His Asn Ile Thr Asp Ile Leu Asp Gly
            20                  25                  30

Tyr Pro Glu Tyr Ser Leu Tyr Asn Ser Tyr Leu Ser Gln Thr Lys Val
        35                  40                  45

Cys Asp Glu Ile Asn Ser Arg Ser Thr Val Thr Cys Leu Val Leu Thr
    50                  55                  60

Asn Gly Ala Met Ser Ser Leu Val Ser Asn Leu Ser Leu Ala Asp Ile
65                  70                  75                  80

Lys Asn Ala Leu Arg Leu Leu Thr Leu Leu Asp Tyr Tyr Asp Thr Lys
                85                  90                  95

Lys Leu His Ser Leu Ser Asp Gly Ser Glu Leu Thr Thr Thr Leu Tyr
            100                 105                 110

Gln Thr Thr Gly Asp Ala Ser Gly Asn Met Gly His Val Asn Ile Thr
        115                 120                 125

Asn Leu Arg Gly Gly Lys Val Gly Phe Ala Ser Ala Ala Pro Gly Ser
    130                 135                 140

Lys Phe Gln Ala Thr Tyr Thr Lys Ser Val Lys Gln Glu Pro Tyr Asn
145                 150                 155                 160

Leu Ser Val Leu Glu Val Ser Asp Pro Ile Thr Phe Pro Gly Leu Phe
                165                 170                 175

Asp Ser Pro Ser Ala Ala Ser Thr Asn Leu Thr Ala Leu Leu Glu Lys
            180                 185                 190

Ala Gly Cys Lys Gln Phe Ala Arg Leu Ile Val Ser Ser Gly Val Met
            195                 200                 205

Lys Met Tyr Gln Ala Ala Met Asp Lys Ala Leu Thr Leu Phe Ala Pro
        210                 215                 220

Asn Asp Asp Ala Phe Gln Ala Lys Gly Leu Pro Asp Leu Ser Lys Leu
225                 230                 235                 240

Thr Ser Ala Glu Leu Val Thr Leu Leu Gln Tyr His Ala Leu Pro Gln
                245                 250                 255

Tyr Ala Pro Lys Ala Ser Leu Lys Thr Ile Lys Gly His Ile Gln Thr
```

-continued

```
                 260             265             270
Leu Ala Ser Thr Gly Ala Gly Lys Tyr Asp Leu Ser Val Val Thr Lys
         275             280             285

Gly Asp Asp Val Ser Met Asp Thr Gly Met Asp Lys Ser Arg Val Ala
     290             295             300

Ser Thr Val Leu Asp Asp Thr Pro Thr Val Ile His Thr Val Asp Ser
305             310             315             320

Val Leu Leu Pro Pro Glu Leu Phe Gly Gly Ala Pro Ser Pro Ala Pro
             325             330             335

Ala Pro Gly Pro Ala Ser Asp Val Pro Ala Ala Ser Pro Ala Pro Glu
         340             345             350

Gly Ser Ser Pro Ala Pro Ser Pro Lys Ala Ala Gly Lys Lys Lys Lys
         355             360             365

Lys Gly Lys Ser Pro Ser His Ser Pro Pro Ala Pro Pro Ala Asp Thr
     370             375             380

Pro Asp Met Ser Pro Ala Asp Ala Pro Ala Gly Glu Glu Ala Ala Asp
385             390             395             400

Lys Ala Glu Lys Lys Asn Gly Ala Thr Ala Ala Ala Thr Ser Val Ala
             405             410             415

Ala Thr Val Ala Ser Ala Ala Ala Leu Leu Ala Ala Ser Phe Leu
             420             425             430

<210> SEQ ID NO 4
<211> LENGTH: 1583
<212> TYPE: DNA
<213> ORGANISM: Artificial Sequence
<220> FEATURE:
<223> OTHER INFORMATION: Laboratory synthesis

<400> SEQUENCE: 4
ctccccaacg tgtcacacca caccacacaa caccaccacc gccgccatgg ccgccaccga      60
ccgccgcctg ctcttcctcc tggccgcctc cctcgccgtc gcggcggtca gctcccacaa     120
catcacggac atcctcgacg gctacccgga gtactcgctg tacaacagct acctctccca     180
gaccaaggtg tgcgacgaga tcaacagccg gagcacggtc acctgcctcg tgctcaccaa     240
cggcgccatg tcctccctcg tctccaacct ctccctcgcc gacatcaaga acgcgctccg     300
cctcctcacc ctcctcgact actacgacac caagaagctg cactccctca gcgacggctc     360
cgagctcacc accacgctgt accagaccac cggcgacgcc tccggtaaca tgggccacgt     420
caacatcacc aacctgcgcg gcggcaaggt tgggttcgcc tccgccgcgc ccggctccaa     480
gttccaggcc acctacacca agtccgtcaa gcaggagccg tacaacctct ccgttcttga     540
ggtctccgac cccatcacct tccccggcct cttcgactcc ccgtcggccg cgtcgaccaa     600
cctcaccgcg cttcttgaga aggccgggtg caagcagttc gcgcggctca tcgtgtcgtc     660
cggggtgatg aagatgtacc aggcggccat ggacaaggcg ctgacgctgt tcgcgcccaa     720
cgacgacgcg ttccaggcca aagggcctgcc ggatctgagc aagctgacca gcgccgagct     780
ggtgacgctt ctgcagtacc acgccttgcc gcagtacgcg cccaaggcgt cgctcaagac     840
catcaagggc cacatccaga ccctggcctc caccggagcg ggtaagtacg acctctccgt     900
cgtcactaag ggcgacgacg tgtccatgga caccggcatg gacaagtccc gcgtcgcgtc     960
caccgtgctg gacgacaccc cgacggttat ccacacggtg gacagcgtgc tgctgccgcc    1020
agagctcttc ggtggcgcac cttccccgc gccggcgccc ggaccggcaa gcgatgtgcc    1080
agccgcttct cccgcgccag aaggctcctc gccggcgccc tcccccaagg cggcgggcaa    1140
```

-continued gaagaaaaag aagggcaagt cgccttccca ttccccaccc gcgcctccgg ccgacacgcc        1200
tgacatgtcg cccgccgacg cgcccgcggg agaagaggct gcagacaaag ccgagaagaa        1260
gaacggcgcc accgcggcgg ccacgagtgt tgcggccact gtggcctccg ccgccgctct        1320
gctcgccgcg tcgttcttgt gagcgtcagg tgttcgacgt tgagctctcg ttgttccccc        1380
ctgggcatgc atggtgtgat gcagtccggt gttcgcttct gagctcgtgg gctccatgga        1440
taatctcatc ctgaagttgt gttcttctct tcctggttgg tagtactcgg tagttagata        1500
ggatttgaat gattgggatc ctcaggtgga gaacggtgat tgtgatgcct attttgttag        1560
agctcggaac catgttttgt ttt                                                1583

<210> SEQ ID NO 5
<211> LENGTH: 1583
<212> TYPE: DNA
<213> ORGANISM: Artificial Sequence
<220> FEATURE:
<223> OTHER INFORMATION: Laboratory synthesis

<400> SEQUENCE: 5
ctccccaacg tgtcacacca caccacacaa caccaccacc gccgccatgg ccgccaccga         60
ccgccgcctg ctcttcctcc tggccgcctc cctcgccgtc gcggcggtca gctcccacaa        120
catcacggac atcctcgacg gctacccgga gtactcgctg tacaacagct acctctccca        180
gaccaaggtg tgcgacgaga tcaacagccg gagcacggtc acctgcctcg tgctcaccaa        240
cggcgccatg tcctccctcg tctccaacct ctccctcgcc gacatcaaga acgcgctccg        300
cctcctcacc ctcctcgact actacgacac caagaagctg cactccctca gcgacggctc        360
cgagctcacc accacgctgt accagaccac cggcgacgcc tccggtaaca tgggccacgt        420
caacatcacc aacctgcgcg gcggcaaggt tgggttcgcc tccgccgcgc ccggctccaa        480
gttccaggcc acctacacca agtccgtcaa gcaggagccg tacaacctct ccgttcttga        540
ggtctccgac cccatcacct tccccggcct cttcgactcc ccgtcggccg cgtcgaccaa        600
cctcaccgcg cttcttgaga aggccggtg caagcagttc gcgcggctca tcgtgtcgtc        660
cggggtgatg aagatgtacc aggcggccat ggacaaggc ctgacgctgt tcgcgcccaa        720
cgacgacgcg ttccaggcca agggcctgcc ggatctgagc aagctgacca gcgccgagct        780
ggtgacgctt ctgcagtacc acgccttgcc gcagtacgcg cccaaggcgt cgctcaagac        840
catcaagggc cacatccaga ccctggcctc caccggagcg ggtaagtacg acctctccgt        900
cgtcactaag ggcgacgacg tgtccatgga caccggcatg gacaagtccc gcgtcgcgtc        960
caccgtgctg gacgacaccc cgacggttat ccacacggtg gacagcgtgc tgctgccgcc        1020
agagctcttc ggtggcgcac cttcccccgc gccggcgccc ggaccggcaa gcgatgtgcc        1080
agccgcttct cccgcgccag aaggctcctc gccggcgccc tcccccaagg cggcgggcaa        1140
gaagaaaaag aagggcaagt cgccttccca ttccccaccc gcgcctccgg ccgacacgcc        1200
tgacatgtcg cccgccgacg cgcccgcggg agaagaggct gcagacaaag ccgagaagaa        1260
gaacggcgcc accgcggcgg ccacgagtgt tgcggccact gtggcctccg ccgccgctct        1320
gctcgccgcg tcgttcttgt gagcgtcagg tgttcgacgt tgagctctcg ttgttccccc        1380
ctgggcatgc atggtgtgat gcagtccggt gttcgcttct gagctcgtgg gctccatgga        1440
taatctcatc ctgaagttgt gttcttctct tcctggttgg tagtactcgg tagttagata        1500
ggatttgaat gattgggatc ctcaggtgga gaacggtgat tgtgatgcct attttgttag        1560

-continued

```
agctcggaac catgttttgt ttt                                          1583

<210> SEQ ID NO 6
<211> LENGTH: 1574
<212> TYPE: DNA
<213> ORGANISM: Artificial Sequence
<220> FEATURE:
<223> OTHER INFORMATION: Laboratory synthesis

<400> SEQUENCE: 6
ctccccaacg tgtcacacca caccacacaa caccaccacc gccgccatgg ccgccaccga     60
ccgccgcctg ctcttcctcc tggccgcctc cctcgccgtc gcggcggtca gctcccacaa    120
catcacggac atcctcgacg gctacccgga gtactcgctg tacctctccc agaccaaggt    180
gtgcgacgag atcaacagcc ggagcacggt cacctgcctc gtgctcacca acggcgccat    240
gtcctccctc gtctccaacc tctccctcgc cgacatcaag aacgcgctcc gcctcctcac    300
cctcctcgac tactacgaca ccaagaagct gcactccctc agcgacggct ccgagctcac    360
caccacgctg taccagacca ccggcgacgc ctccggtaac atgggccacg tcaacatcac    420
caacctgcgc ggcggcaagg ttgggttcgc ctccgccgcg cccggctcca agttccaggc    480
cacctacacc aagtccgtca agcaggagcc gtacaacctc tccgttcttg aggtctccga    540
ccccatcacc ttccccggcc tcttcgactc cccgtcggcc gcgtcgacca acctcaccgc    600
gcttcttgag aaggccgggt gcaagcagtt cgcgcggctc atcgtgtcgt ccggggtgat    660
gaagatgtac caggcggcca tggacaaggc gctgacgctg ttcgcgccca cgacgacgc     720 gttccaggcc aagggcctgc cggatctgag caagctgacc agcgccgagc tggtgacgct    780
tctgcagtac cacgccttgc cgcagtacgc gcccaaggcg tcgctcaaga ccatcaaggg    840
ccacatccag accctggcct ccaccggagc gggtaagtac gacctctccg tcgtcactaa    900
gggcgacgac gtgtccatgg acaccggcat ggacaagtcc cgcgtcgcgt ccaccgtgct    960
ggacgacacc ccgacggtta tccacacggt ggacagcgtg ctgctgccgc cagagctctt   1020
cggtggcgca ccttcccccg cgccggcgcc cggaccggca agcgatgtgc cagccgcttc   1080
tcccgcgcca gaaggctcct cgccggcgcc ctccccaag gcggcgggca agaagaaaaa    1140
gaagggcaag tcgccttccc attccccacc cgcgcctccg gccgacacgc ctgacatgtc   1200
gcccgccgac gcgcccgcgg gagaagaggc tgcagacaaa gccgagaaga agaacggcgc   1260
caccgcggcg gccacgagtg ttgcggccac tgtggcctcc gccgccgctc tgctcgccgc   1320
gtcgttcttg tgagcgtcag gtgttcgacg ttgagctctc gttgttcccc cctgggcatg   1380
catggtgtga tgcagtccgg tgttcgcttc tgagctcgtg ggctccatgg ataatctcat   1440
cctgaagttg tgttcttctc ttcctggttg gtagtactcg gtagttagat aggatttgaa   1500
tgattgggat cctcaggtgg agaacggtga ttgtgatgcc tattttgtta gagctcggaa   1560
ccatgttttg tttt                                                   1574

<210> SEQ ID NO 7
<211> LENGTH: 1287
<212> TYPE: DNA
<213> ORGANISM: Artificial Sequence
<220> FEATURE:
<223> OTHER INFORMATION: Laboratory synthesis

<400> SEQUENCE: 7
atggccgcca ccgaccgccg cctgctcttc ctcctggccg cctccctcgc cgtcgcggcg     60
gtcagctccc acaacatcac ggacatcctc gacggctacc cggagtactc gctgtacctc    120
```

-continued

```
tcccagacca aggtgtgcga cgagatcaac agccggagca cggtcacctg cctcgtgctc      180
accaacggcg ccatgtcctc cctcgtctcc aacctctccc tcgccgacat caagaacgcg      240
ctccgcctcc tcaccctcct cgactactac gacaccaaga agctgcactc cctcagcgac      300
ggctccgagc tcaccaccac gctgtaccag accaccggcg acgcctccgg taacatgggc      360
cacgtcaaca tcaccaacct gcgcggcggc aaggttgggt cgcctccgc cgcgcccggc       420 tccaagttcc aggccaccta caccaagtcc gtcaagcagg agccgtacaa cctctccgtt      480
cttgaggtct ccgaccccat caccttcccc ggcctcttcg actcccccgtc ggccgcgtcg     540 accaacctca ccgcgcttct tgagaaggcc gggtgcaagc agttcgcgcg gctcatcgtg      600
tcgtccgggg tgatgaagat gtaccaggcg gccatggaca aggcgctgac gctgttcgcg      660
cccaacgacg acgcgttcca ggccaagggc ctgccggatc tgagcaagct gaccagcgcc      720
gagctggtga cgcttctgca gtaccacgcc ttgccgcagt acgcgcccaa ggcgtcgctc      780
aagaccatca agggccacat ccagaccctg gcctccaccg gagcgggtaa gtacgacctc      840
tccgtcgtca ctaagggcga cgacgtgtcc atggacaccg gcatggacaa gtcccgcgtc      900
gcgtccaccg tgctggacga cacccccgacg gttatccaca cggtggacag cgtgctgctg      960
ccgccagagc tcttcggtgg cgcaccttcc cccgcgccgg cgcccggacc ggcaagcgat      1020
gtgccagccg cttctcccgc gccagaaggc tcctcgccgg cgccctcccc caaggcggcg      1080
ggcaagaaga aaaagaaggg caagtcgcct tcccattccc cacccgcgcc tccggccgac      1140
acgcctgaca tgtcgcccgc cgacgcgccc gcgggagaag aggctgcaga caaagccgag      1200
aagaagaacg gcgccaccgc ggcggccacg agtgttgcgg ccactgtggc ctccgccgcc      1260
gctctgctcg ccgcgtcgtt cttgtga                                         1287
```

<210> SEQ ID NO 8
<211> LENGTH: 428
<212> TYPE: PRT
<213> ORGANISM: Artificial Sequence
<220> FEATURE:
<223> OTHER INFORMATION: Laboratory synthesis

<400> SEQUENCE: 8

```
Met Ala Ala Thr Asp Arg Arg Leu Leu Phe Leu Leu Ala Ala Ser Leu
1               5                   10                  15

Ala Val Ala Ala Val Ser Ser His Asn Ile Thr Asp Ile Leu Asp Gly
            20                  25                  30

Tyr Pro Glu Tyr Ser Leu Tyr Leu Ser Gln Thr Lys Val Cys Asp Glu
        35                  40                  45

Ile Asn Ser Arg Ser Thr Val Thr Cys Leu Val Leu Thr Asn Gly Ala
    50                  55                  60

Met Ser Ser Leu Val Ser Asn Leu Ser Leu Ala Asp Ile Lys Asn Ala
65                  70                  75                  80

Leu Arg Leu Leu Thr Leu Leu Asp Tyr Tyr Asp Thr Lys Lys Leu His
                85                  90                  95

Ser Leu Ser Asp Gly Ser Glu Leu Thr Thr Thr Leu Tyr Gln Thr Thr
            100                 105                 110

Gly Asp Ala Ser Gly Asn Met Gly His Val Asn Ile Thr Asn Leu Arg
        115                 120                 125

Gly Gly Lys Val Gly Phe Ala Ser Ala Ala Pro Gly Ser Lys Phe Gln
    130                 135                 140

Ala Thr Tyr Thr Lys Ser Val Lys Gln Glu Pro Tyr Asn Leu Ser Val
```

-continued

```
145              150              155              160

Leu Glu Val Ser Asp Pro Ile Thr Phe Pro Gly Leu Phe Asp Ser Pro
              165              170              175

Ser Ala Ala Ser Thr Asn Leu Thr Ala Leu Leu Glu Lys Ala Gly Cys
              180              185              190

Lys Gln Phe Ala Arg Leu Ile Val Ser Ser Gly Val Met Lys Met Tyr
              195              200              205

Gln Ala Ala Met Asp Lys Ala Leu Thr Leu Phe Ala Pro Asn Asp Asp
     210              215              220

Ala Phe Gln Ala Lys Gly Leu Pro Asp Leu Ser Lys Leu Thr Ser Ala
225              230              235              240

Glu Leu Val Thr Leu Leu Gln Tyr His Ala Leu Pro Gln Tyr Ala Pro
              245              250              255

Lys Ala Ser Leu Lys Thr Ile Lys Gly His Ile Gln Thr Leu Ala Ser
              260              265              270

Thr Gly Ala Gly Lys Tyr Asp Leu Ser Val Val Thr Lys Gly Asp Asp
              275              280              285

Val Ser Met Asp Thr Gly Met Asp Lys Ser Arg Val Ala Ser Thr Val
     290              295              300

Leu Asp Asp Thr Pro Thr Val Ile His Thr Val Asp Ser Val Leu Leu
305              310              315              320

Pro Pro Glu Leu Phe Gly Gly Ala Pro Ser Pro Ala Pro Ala Pro Gly
              325              330              335

Pro Ala Ser Asp Val Pro Ala Ala Ser Pro Ala Pro Glu Gly Ser Ser
              340              345              350

Pro Ala Pro Ser Pro Lys Ala Ala Gly Lys Lys Lys Lys Gly Lys
              355              360              365

Ser Pro Ser His Ser Pro Pro Ala Pro Pro Ala Asp Thr Pro Asp Met
     370              375              380

Ser Pro Ala Asp Ala Pro Ala Gly Glu Glu Ala Ala Asp Lys Ala Glu
385              390              395              400

Lys Lys Asn Gly Ala Thr Ala Ala Ala Thr Ser Val Ala Ala Thr Val
              405              410              415

Ala Ser Ala Ala Ala Leu Leu Ala Ala Ser Phe Leu
              420              425
```

```
<210> SEQ ID NO 9
<211> LENGTH: 424
<212> TYPE: PRT
<213> ORGANISM: Artificial Sequence
<220> FEATURE:
<223> OTHER INFORMATION: Laboratory synthesis

<400> SEQUENCE: 9

Met Ala Val Ser Arg Ala Phe Ser Leu Phe Ala Phe Thr Leu Ser Leu
1               5               10              15

Leu Ala Val Ala Tyr Thr Val Ser Gly His Asn Ile Thr Gln Ile Leu
              20              25              30

Ser Asp Thr Pro Glu Tyr Ser Ser Phe Asn Asn Tyr Leu Ser Gln Thr
          35              40              45

Lys Leu Ala Asp Glu Ile Asn Ser Arg Thr Thr Ile Thr Val Leu Val
     50              55              60

Leu Asn Asn Gly Ala Met Ser Ser Leu Ala Gly Lys His Pro Leu Ser
65              70              75              80

Val Val Lys Asn Ala Leu Ser Leu Leu Val Leu Leu Asp Tyr Tyr Asp
```

```
                85                  90                  95

Pro Leu Lys Leu His Gln Leu Ala Lys Gly Ser Thr Leu Thr Thr Thr
            100                 105                 110

Leu Tyr Gln Thr Thr Gly His Ala Pro Gly Asn Leu Gly Phe Val Asn
            115                 120                 125

Val Thr Asp Leu Lys Gly Gly Lys Val Gly Phe Gly Ser Ala Ala Pro
            130                 135                 140

Gly Ser Lys Leu Asp Ser Ser Tyr Thr Lys Ser Val Lys Gln Ile Pro
145                 150                 155                 160

Tyr Asn Ile Ser Val Leu Glu Ile Asn Ala Pro Ile Ile Ala Pro Gly
                165                 170                 175

Ile Leu Thr Ala Ala Ala Pro Ser Ser Gly Gly Val Asn Asn Leu Thr
            180                 185                 190

Gly Leu Leu Glu Lys Ala Gly Cys Lys Thr Phe Ala Asn Leu Leu Val
            195                 200                 205

Ser Ser Gly Val Leu Lys Thr Tyr Glu Ser Thr Val Glu Lys Gly Leu
    210                 215                 220

Thr Val Phe Ala Pro Ser Asp Glu Ala Phe Lys Ala Lys Gly Val Pro
225                 230                 235                 240

Asp Leu Thr Asn Leu Thr Gln Ala Glu Val Val Ser Leu Leu Glu Tyr
                245                 250                 255

His Ala Leu Ala Glu Tyr Lys Pro Lys Gly Ser Leu Lys Thr Asn Lys
            260                 265                 270

Asp Ala Ile Ser Thr Leu Ala Thr Asn Gly Ala Gly Lys Tyr Asp Leu
            275                 280                 285

Thr Thr Ser Thr Ser Gly Asp Glu Val Ile Leu His Thr Gly Val Gly
    290                 295                 300

Pro Ser Arg Leu Ala Asp Thr Val Val Asp Glu Thr Pro Val Val Ile
305                 310                 315                 320

Phe Thr Val Asp Asn Val Leu Leu Pro Thr Glu Leu Phe Gly Lys Ser
                325                 330                 335

Pro Ser Pro Ala Pro Ala Pro Ala Pro Glu Pro Val Ser Ala Pro Thr
            340                 345                 350

Pro Ser Pro Ala Asn Ala Pro Ser Pro Val Glu Ala Pro Ser Pro Thr
            355                 360                 365

Ala Ala Ser Pro Pro Ala Pro Pro Val Asp Glu Ser Ser Pro Glu Gly
    370                 375                 380

Ala Pro Ser Asp Ser Pro Thr Ser Ser Glu Asn Ser Asn Ala Lys Asn
385                 390                 395                 400

Ala Ala Leu His Val Thr Ala Pro Ala Leu Phe Thr Ala Leu Val Thr
                405                 410                 415

Leu Ala Ala Thr Ser Leu Leu Ser
            420

<210> SEQ ID NO 10
<211> LENGTH: 420
<212> TYPE: PRT
<213> ORGANISM: Artificial Sequence
<220> FEATURE:
<223> OTHER INFORMATION: Laboratory synthesis

<400> SEQUENCE: 10

Met Ile Ser Ser Val Leu Leu Leu Leu Val Leu Leu Cys Gly Pro Trp
1               5                   10                  15

Ala Gly Cys Arg Ala His Asn Ile Thr Ala Ile Leu Glu Arg Tyr Pro
```

-continued

```
                 20                  25                  30

Glu Tyr Thr Leu Tyr Asn Ser Tyr Leu Thr Arg Thr Lys Val Cys Asp
             35                  40                  45

Glu Ile Asn Ala His Glu Thr Val Thr Cys Leu Val Leu Asp Asp Gly
         50                  55                  60

Ala Met Ser Thr Leu Ala Ala Lys Arg Pro Leu Ala Ala Ile Lys Asn
65                  70                  75                  80

Ala Leu Arg Leu Leu Ala Leu Leu Asp Tyr Phe Asp Pro Pro Lys Leu
                 85                  90                  95

His Ala Leu Ser Ser Gly Thr Thr Leu Thr Thr Thr Leu Leu Gln Thr
             100                 105                 110

Thr Gly Asn Glu Ala Gly Asn Leu Gly Phe Val Asn Ile Thr Asn Leu
         115                 120                 125

Arg Gly Gly Arg Val Gly Phe Ala Ser Thr Ala Pro Gly Ser Lys Phe
         130                 135                 140

Asp Ser Thr Tyr Thr Lys Ser Ile Glu Gln Ile Pro Tyr Asn Leu Ser
145                 150                 155                 160

Val Leu Ala Val Ser Ala Pro Ile Val Phe Pro Gly Leu Leu Asp Thr
                 165                 170                 175

Pro Thr Ala Ala Ser Ser Asn Leu Thr Ala Leu Leu Glu Lys Ala Gly
             180                 185                 190

Cys Lys Thr Phe Ala Arg Leu Leu Thr Thr Ser Gly Val Leu Lys Val
             195                 200                 205

Phe Gln Asp Ala Met Ala Lys Gly Leu Thr Leu Phe Ala Pro Asn Asp
         210                 215                 220

Glu Ala Phe Lys Ala Thr Asp Ala Pro Asp Leu Asn Ser Leu Ser Ser
225                 230                 235                 240

Ala Glu Leu Val Thr Leu Leu Gln Tyr His Ala Leu Pro Ser Tyr Thr
                 245                 250                 255

Pro Lys Ala Ser Leu Lys Ser Val Gly Gly Arg Leu Pro Thr Met Ala
             260                 265                 270

Ser Ser Ala Ala Gly Lys Tyr Asp Leu Ser Val Val Ser Arg Gly Asp
             275                 280                 285

Asp Val Ser Leu Asp Thr Gly Val Asp Thr Ser Arg Val Ala Ser Thr
         290                 295                 300

Val Leu Asp Asp Thr Pro Val Cys Ile Leu Thr Val Asp Asn Leu Leu
305                 310                 315                 320

Leu Pro Ile Glu Leu Phe Gly Ala Ala Pro Ser Pro Ala Pro Thr Pro
             325                 330                 335

Ser Pro Ser Thr Ser Pro Val Glu Ala Pro Ala Pro Thr Pro Val Ala
             340                 345                 350

Lys Ala Pro Ser Pro Lys Ser His Lys Lys His His Ser Pro Pro Ala
             355                 360                 365

Pro Pro Met Ala Ser Pro Glu Ser Ala Pro Ser Asp Ala Pro Ala Ala
         370                 375                 380

Ala Ala Asp Lys Ala Asp Val Lys Ser Ala Val Gly Val Ala Thr Pro
385                 390                 395                 400

Ile Gly Thr Leu Ala Thr Val Ala Val Val Leu Ala Thr Leu Ala Met
                 405                 410                 415

Ala Ser Leu Pro
             420
```

<210> SEQ ID NO 11

-continued

```
<211> LENGTH: 431
<212> TYPE: PRT
<213> ORGANISM: Artificial Sequence
<220> FEATURE:
<223> OTHER INFORMATION: Laboratory synthesis

<400> SEQUENCE: 11

Met Ala Ala Thr Asp Arg Arg Leu Leu Phe Leu Leu Ala Ala Ser Leu
1               5                   10                  15

Ala Val Ala Ala Val Ser Ser His Asn Ile Thr Asp Ile Leu Asp Gly
                20                  25                  30

Tyr Pro Glu Tyr Ser Leu Tyr Asn Ser Tyr Leu Ser Gln Thr Lys Val
            35                  40                  45

Cys Asp Glu Ile Asn Ser Arg Ser Thr Val Thr Cys Leu Val Leu Thr
        50                  55                  60

Asn Gly Ala Met Ser Ser Leu Val Ser Asn Leu Ser Leu Ala Asp Ile
65                  70                  75                  80

Lys Asn Ala Leu Arg Leu Leu Thr Leu Leu Asp Tyr Tyr Asp Thr Lys
                85                  90                  95

Lys Leu His Ser Leu Ser Asp Gly Ser Glu Leu Thr Thr Thr Leu Tyr
            100                 105                 110

Gln Thr Thr Gly Asp Ala Ser Gly Asn Met Gly His Val Asn Ile Thr
            115                 120                 125

Asn Leu Arg Gly Gly Lys Val Gly Phe Ala Ser Ala Ala Pro Gly Ser
        130                 135                 140

Lys Phe Gln Ala Thr Tyr Thr Lys Ser Val Lys Gln Glu Pro Tyr Asn
145                 150                 155                 160

Leu Ser Val Leu Glu Val Ser Asp Pro Ile Thr Phe Pro Gly Leu Phe
                165                 170                 175

Asp Ser Pro Ser Ala Ala Ser Thr Asn Leu Thr Ala Leu Leu Glu Lys
            180                 185                 190

Ala Gly Cys Lys Gln Phe Ala Arg Leu Ile Val Ser Ser Gly Val Met
            195                 200                 205

Lys Met Tyr Gln Ala Ala Met Asp Lys Ala Leu Thr Leu Phe Ala Pro
        210                 215                 220

Asn Asp Asp Ala Phe Gln Ala Lys Gly Leu Pro Asp Leu Ser Lys Leu
225                 230                 235                 240

Thr Ser Ala Glu Leu Val Thr Leu Leu Gln Tyr His Ala Leu Pro Gln
                245                 250                 255

Tyr Ala Pro Lys Ala Ser Leu Lys Thr Ile Lys Gly His Ile Gln Thr
            260                 265                 270

Leu Ala Ser Thr Gly Ala Gly Lys Tyr Asp Leu Ser Val Val Thr Lys
        275                 280                 285

Gly Asp Asp Val Ser Met Asp Thr Gly Met Asp Lys Ser Arg Val Ala
    290                 295                 300

Ser Thr Val Leu Asp Asp Thr Pro Thr Val Ile His Thr Val Asp Ser
305                 310                 315                 320

Val Leu Leu Pro Pro Glu Leu Phe Gly Gly Ala Pro Ser Pro Ala Pro
                325                 330                 335

Ala Pro Gly Pro Ala Ser Asp Val Pro Ala Ala Ser Pro Ala Pro Glu
            340                 345                 350

Gly Ser Ser Pro Ala Pro Ser Pro Lys Ala Ala Gly Lys Lys Lys Lys
            355                 360                 365

Lys Gly Lys Ser Pro Ser His Ser Pro Pro Ala Pro Pro Ala Asp Thr
        370                 375                 380
```

```
Pro Asp Met Ser Pro Ala Asp Ala Pro Ala Gly Glu Glu Ala Ala Asp
385                 390             395                 400

Lys Ala Glu Lys Lys Asn Gly Ala Thr Ala Ala Ala Thr Ser Val Ala
                405             410             415

Ala Thr Val Ala Ser Ala Ala Ala Leu Leu Ala Ala Ser Phe Leu
            420             425             430

<210> SEQ ID NO 12
<211> LENGTH: 431
<212> TYPE: PRT
<213> ORGANISM: Artificial Sequence
<220> FEATURE:
<223> OTHER INFORMATION: Laboratory synthesis

<400> SEQUENCE: 12

Met Ala Ala Pro Asp Arg Arg Leu Leu Phe Leu Leu Ala Val Ser Leu
1               5               10              15

Ala Val Ala Ala Val Ser Ser His Asn Ile Thr Asp Ile Leu Asp Gly
            20              25              30

Tyr Pro Glu Tyr Ser Leu Tyr Asn Ser Tyr Leu Ser Gln Thr Lys Val
        35              40              45

Cys Asp Glu Ile Asn Ser Arg Ser Thr Val Thr Cys Leu Val Leu Thr
    50              55              60

Asn Gly Ala Met Ser Ser Leu Val Ser Asn Leu Ser Leu Ala Asp Ile
65              70              75              80

Lys Asn Ala Leu Arg Leu Leu Thr Leu Leu Asp Tyr Tyr Asp Thr Lys
            85              90              95

Lys Leu His Ser Leu Ser Asp Gly Ser Glu Leu Thr Thr Thr Leu Tyr
            100             105             110

Gln Thr Thr Gly Asp Ala Ser Gly Asn Met Gly His Val Asn Ile Thr
            115             120             125

Asn Leu Arg Gly Gly Lys Val Gly Phe Ala Ser Ala Ala Pro Gly Ser
    130             135             140

Lys Phe Gln Ala Thr Tyr Thr Lys Ser Val Lys Gln Glu Pro Tyr Asn
145             150             155             160

Leu Ser Val Leu Glu Val Ser Asp Pro Ile Thr Phe Pro Gly Leu Phe
            165             170             175

Asn Ser Pro Ser Ala Ala Ser Thr Asn Leu Thr Ala Leu Leu Glu Lys
            180             185             190

Ala Gly Cys Lys Gln Phe Ala Arg Leu Ile Val Ser Ser Gly Val Ile
            195             200             205

Lys Met Tyr Gln Ala Ala Met Asp Lys Gly Leu Thr Leu Phe Ala Pro
    210             215             220

Asn Asp Asp Ala Phe His Ala Lys Asp Leu Pro Asp Leu Ser Lys Leu
225             230             235             240

Thr Ser Ala Glu Leu Val Thr Leu Leu Gln Tyr His Ala Leu Pro Gln
            245             250             255

Tyr Ala Pro Lys Ala Ser Leu Lys Thr Ile Lys Gly Asn Leu Gln Thr
            260             265             270

Leu Ala Ser Thr Gly Ala Gly Lys Tyr Asp Leu Ser Val Val Ala Lys
            275             280             285

Gly Asp Asp Val Ser Met Asp Thr Gly Val Asp Lys Ser Arg Val Ala
    290             295             300

Ser Thr Val Leu Asp Asp Thr Pro Thr Val Ile His Thr Val Asp Ser
305             310             315             320
```

-continued

```
Val Leu Leu Pro Arg Glu Leu Phe Gly Gly Ala Pro Ser Pro Ala Pro
            325             330             335

Ala Ala Gly Pro Ala Ser Asp Val Pro Ala Ala Ser Pro Ala Pro Glu
            340             345             350

Gly Ser Ser Pro Ala Pro Ser Pro Lys Ala Ala Gly Lys Lys Lys Lys
            355             360             365

Lys Gly Lys Ser Pro Ser His Ser Pro Pro Ala Pro Pro Ala Asp Thr
        370             375             380

Pro Asp Met Ser Pro Ala Asp Ala Pro Gln Gly Glu Glu Ala Ala Asp
385             390             395             400

Lys Ala Val Lys Lys Asn Gly Ala Thr Ala Val Ala Thr Ser Val Ala
            405             410             415

Thr Thr Val Ala Ser Val Ala Val Leu Leu Ala Ala Ser Phe Leu
            420             425             430
```

```
<210> SEQ ID NO 13
<211> LENGTH: 429
<212> TYPE: PRT
<213> ORGANISM: Artificial Sequence
<220> FEATURE:
<223> OTHER INFORMATION: Laboratory synthesis

<400> SEQUENCE: 13
```

```
Met Ala Ala Gly Arg Arg Leu Leu Val Leu Leu Ala Val Ser Leu Ala
1               5               10              15

Ala Val Ala Ala Thr Arg Gly His Asn Ile Thr Glu Ile Leu Asp Gly
            20              25              30

Tyr Ser Glu Tyr Ser Leu Tyr Asn Asn Tyr Leu Ser Gln Thr Lys Val
        35              40              45

Cys Asp Glu Ile Asn Ser Arg Ser Thr Val Thr Ser Leu Val Leu Thr
    50              55              60

Asn Gly Ala Met Ser Ser Leu Val Ala Asn Leu Ser Leu Ala Asp Val
65              70              75              80

Lys Asn Ala Leu Arg Leu Leu Thr Leu Leu Asp Tyr Tyr Asp Pro Lys
            85              90              95

Lys Leu His Ser Leu His Gly Gly Ser Glu Leu Thr Thr Thr Leu Tyr
            100             105             110

Gln Thr Thr Gly Asp Ala Ser Gly Asp Met Gly His Val Asn Ile Thr
        115             120             125

Ser Leu Arg Gly Gly Lys Val Gly Phe Ala Ser Ala Glu Pro Gly Ser
    130             135             140

Lys Phe Gln Ala Thr Tyr Thr Lys Ser Ile Lys Glu Glu Pro Tyr Asn
145             150             155             160

Leu Ser Val Leu Glu Val Ser Asp Pro Ile Thr Phe Pro Gly Leu Phe
            165             170             175

Ser Ser Pro Ser Ala Ala Ser Thr Asn Leu Thr Ala Leu Leu Glu Lys
            180             185             190

Ala Gly Cys Lys His Phe Ala Arg Leu Ile Val Ser Ser Gly Val Ile
            195             200             205

Lys Thr Tyr Gln Ala Ala Met Asp Lys Gly Leu Thr Leu Phe Ala Pro
        210             215             220

Asn Asp Asp Ala Phe Gln Ala Lys Gly Leu Pro Asp Leu Ser Lys Leu
225             230             235             240

Ser Ser Ala Asp Leu Val Ala Leu Leu Glu Tyr His Ala Leu Pro Gln
            245             250             255
```

```
Tyr Ala Pro Lys Ala Ser Leu Lys Thr Met Lys Gly Gly Ile Pro Thr
        260                 265                 270

Leu Ala Ser Thr Gly Lys Gly Lys Tyr Asp Leu Ser Val Val Ala Lys
        275                 280                 285

Gly Asp Asp Val Ser Met Asp Thr Gly Met Asp Lys Ser Arg Val Ala
        290                 295                 300

Ser Thr Val Leu Asp Asp Thr Pro Val Thr Val His Thr Val Asp Ser
305                 310                 315                 320

Val Leu Leu Pro Pro Glu Leu Phe Gly Gly Ala Pro Ser Pro Ala Pro
                325                 330                 335

Gly Ala Ser Ala Asp Ser Pro Ala Ser Ala Pro Ala Pro Glu Thr Ser
        340                 345                 350

Ala Pro Ala Pro Ser Pro Lys His Asp Lys Lys Lys Pro Lys Gly Lys
        355                 360                 365

Ser Pro Ala His Ser Pro Pro Ala Pro Pro Ala Asp Ser Pro Asp Asn
        370                 375                 380

Ala Pro Ala Asp Ala Pro Asp Gly Glu Gly Asp Glu Glu Ala Asp Lys
385                 390                 395                 400

Ala Asp Ser Lys Asn Gly Ala Thr Ala Val Gly Met Ser Ile Ala Ala
                405                 410                 415

Met Val Ala Ser Val Ala Leu Val Gly Ala Ser Leu Leu
                420                 425
```

```
<210> SEQ ID NO 14
<211> LENGTH: 429
<212> TYPE: PRT
<213> ORGANISM: Artificial Sequence
<220> FEATURE:
<223> OTHER INFORMATION: Laboratory synthesis

<400> SEQUENCE: 14

Met Ala Ala Ser His His Leu Ile Leu Leu Val Leu Cys Leu Thr Ala
1                   5                   10                  15

Ala Ala Ala Ser Ala His Asn Ile Thr Ala Ile Leu Asp Gly Arg Ser
                20                  25                  30

Glu Tyr Thr Leu Tyr Asn Ser Tyr Leu Ser Gln Thr Lys Val Cys Asp
                35                  40                  45

Glu Ile Asn Ser Arg Ser Ser Val Thr Val Leu Val Leu Thr Asn Gly
        50                  55                  60

Ala Met Ser Ser Leu Val Ala Asn Leu Ser Leu Ala Asp Ile Lys Asn
65                  70                  75                  80

Ala Leu Arg Leu Leu Thr Leu Leu Asp Tyr Phe Asp Glu Lys Lys Leu
                85                  90                  95

His Ser Ile Gly Ser Ser Ser Gln Leu Thr Thr Ser Leu Tyr Gln Thr
                100                 105                 110

Thr Gly Gln Ala Ala Gly Asp Met Gly His Val Asn Ile Thr Asp Leu
        115                 120                 125

Arg Gly Gly Lys Val Ala Phe Ala Ser Ala Ala Pro Gly Ala Lys Phe
        130                 135                 140

Gln Ser Thr Tyr Thr Lys Arg Val Ala Asp Phe Pro Ser Asn Leu Ser
145                 150                 155                 160

Val Leu Glu Val Ser Asp Pro Ile Thr Phe Pro Gly Leu Phe Gly Ser
                165                 170                 175

Pro Ser Ala Ser Ser Ala Asn Ile Thr Asp Leu Leu Glu Lys Ala Gly
        180                 185                 190
```

-continued

```
Cys Lys Gln Phe Ala Arg Leu Ile Val Ser Ser Gly Val Val Lys Thr
        195                 200                 205

Tyr Gln Ala Ala Met Asp Lys Gly Leu Thr Leu Phe Ala Pro Asn Asp
    210                 215                 220

Asp Ala Phe Lys Ala Lys Asp Leu Pro Asp Leu Ser Lys Leu Thr Ser
225                 230                 235                 240

Ala Asp Leu Val Ala Leu Leu Gln Tyr His Ala Leu Pro Gln Tyr Ala
                245                 250                 255

Pro Lys Ala Ser Leu Lys Val Ala Ser Gly Arg Ile Pro Thr Leu Ala
                260                 265                 270

Ser Thr Gly Ala Gly Lys Tyr Asp Leu Thr Val Ala Ser Ser Gly Asp
                275                 280                 285

Glu Val Ser Leu Asp Thr Gly Val Asp Lys Ser Arg Val Ala Ser Thr
    290                 295                 300

Val Leu Asp Asp Pro Pro Thr Val Ile Leu Thr Val Asp Ser Val Leu
305                 310                 315                 320

Leu Pro His Val Ile Phe Gly Gly Ala Pro Ser Pro Ala Pro Ala Pro
                325                 330                 335

Gly Pro Ala Ala Asp Val Pro Ala Ser Ala Pro Ala Pro Glu Gly Ser
                340                 345                 350

Ala Pro Ala Pro Thr Pro Lys Ala Ala Gly Lys Lys Lys Lys Lys Lys
                355                 360                 365

Ala Lys Ser Pro Ser His Ser Pro Pro Ala Pro Pro Ala Asp Ser Pro
    370                 375                 380

Asp Leu Ala Pro Ala Asp Ala Pro Asp Asp Asp Ala Ala Asp Lys Val
385                 390                 395                 400

Glu Ser Lys Lys Asn Gly Ala Ala Ala Ala Val Ser Phe Val Ala
                405                 410                 415

Ser Val Ala Ser Ala Gly Leu Ala Val Ala Leu Leu Leu
            420                 425
```

```
<210> SEQ ID NO 15
<211> LENGTH: 429
<212> TYPE: PRT
<213> ORGANISM: Artificial Sequence
<220> FEATURE:
<223> OTHER INFORMATION: Laboratory synthesis

<400> SEQUENCE: 15
```

```
Met Ala Ala Ser His Arg Leu Ile Leu Leu Val Leu Cys Leu Thr Ala
1               5                   10                  15

Thr Ala Ala Ser Ala His Asn Ile Thr Ala Ile Leu Asp Gly Arg Ser
                20                  25                  30

Glu Tyr Thr Leu Tyr Asn Ser Tyr Leu Ser Glu Thr Lys Val Cys Asp
            35                  40                  45

Glu Ile Asn Ser Arg Ser Ser Val Thr Val Leu Val Leu Thr Asn Gly
    50                  55                  60

Ala Met Ser Ser Leu Val Ala Asn Leu Ser Leu Ala Asp Ile Lys Asn
65                  70                  75                  80

Ala Leu Arg Leu Leu Thr Leu Leu Asp Tyr Phe Asp Glu Lys Lys Leu
                85                  90                  95

His Ser Ile Gly Ser Ser Ser Gln Leu Thr Thr Ser Leu Tyr Gln Thr
            100                 105                 110

Thr Gly Gln Ala Ala Gly Asp Met Gly His Val Asn Ile Thr Asp Leu
            115                 120                 125
```

Arg Gly Gly Lys Val Ala Phe Ala Ser Ala Ala Pro Gly Ala Lys Phe
    130                 135                 140

Gln Ser Thr Tyr Thr Lys Arg Val Ala Asp Phe Pro Ser Asn Leu Ser
145                 150                 155                 160

Val Leu Glu Val Ser Asp Pro Ile Thr Phe Pro Gly Leu Phe Gly Ala
                165                 170                 175

Pro Ser Ala Ser Ser Ala Asn Ile Thr Asp Leu Leu Glu Lys Ala Gly
                180                 185                 190

Cys Lys Gln Phe Ala Arg Leu Ile Val Ser Ser Gly Val Val Lys Thr
            195                 200                 205

Tyr Gln Ala Ala Met Asp Lys Ala Leu Thr Leu Phe Ala Pro Asn Asp
    210                 215                 220

Asp Ala Phe Lys Ala Lys Asp Leu Pro Asp Leu Ser Lys Leu Thr Ser
225                 230                 235                 240

Ala Asp Leu Val Ala Leu Leu Gln Tyr His Ala Leu Pro Gln Tyr Ala
                245                 250                 255

Pro Lys Ala Ser Leu Lys Val Ala Ser Gly Arg Ile Pro Thr Leu Ala
                260                 265                 270

Ser Thr Ala Ala Gly Lys Tyr Asp Leu Ala Val Ala Ser Ser Gly Asp
            275                 280                 285

Glu Val Thr Leu Asp Thr Gly Val Asp Lys Ser Arg Ile Ala Ser Thr
    290                 295                 300

Val Leu Asp Asp Pro Pro Thr Val Ile Leu Thr Val Asp Ser Val Leu
305                 310                 315                 320

Leu Pro His Val Leu Phe Gly Gly Ala Pro Ser Pro Ala Pro Ala Pro
                325                 330                 335

Gly Pro Ala Ala Asp Val Pro Ala Ser Ala Pro Ala Pro Glu Gly Ser
            340                 345                 350

Ala Pro Ala Pro Ala Pro Lys Ala Ala Gly Lys Arg Lys Lys Lys Lys
            355                 360                 365

Ala Arg Ser Pro Ser His Ser Pro Pro Ala Pro Pro Ala Asp Ser Pro
    370                 375                 380

Asp Met Ala Pro Ala Asp Ala Pro Thr Glu Asp Ala Ala Asp Lys Val
385                 390                 395                 400

Glu Ser Lys Lys Asn Gly Gly Ala Ala Ala Ala Val Ser Phe Ala Ala
            405                 410                 415

Ser Val Ala Ser Val Ala Leu Ala Val Ala Tyr Leu Leu
            420                 425

<210> SEQ ID NO 16
<211> LENGTH: 430
<212> TYPE: PRT
<213> ORGANISM: Artificial Sequence
<220> FEATURE:
<223> OTHER INFORMATION: Laboratory synthesis

<400> SEQUENCE: 16

Met Ala Ala Ser His His Gly His Phe Phe Leu Leu Ala Leu Ser Ala
1               5                   10                  15

Ala Ala Asp Ser Ser Ser Thr His Asn Ile Thr Thr Val Leu Asp Gly
                20                  25                  30

Arg Ser Glu Tyr Thr Leu Tyr Asn Ser Tyr Leu Ser Glu Thr Lys Val
        35                  40                  45

Cys Asp Glu Ile Asn Ser Glu His Thr Val Thr Val Leu Val Leu Thr
    50                  55                  60

-continued

```
Asn Gly Ala Met Ser Ser Leu Val Ala Asn Leu Ser Leu Ala Asp Ile
65                  70                  75                  80

Lys Asn Ala Leu Arg Leu Leu Thr Leu Leu Asp Tyr Phe Asp Glu Lys
                85                  90                  95

Lys Leu His Ser Leu Asp Ser Gly Ser Glu Leu Thr Thr Ser Leu Tyr
            100                 105                 110

Gln Lys Thr Gly Gln Ala Ala Gly Asn Met Gly His Val Asn Ile Thr
            115                 120                 125

Asp Leu Arg Gly Gly Lys Val Gly Phe Ala Pro Ala Ala Pro Gly Ala
        130                 135                 140

Lys Phe Gln Ser Thr Tyr Thr Lys Arg Val Asp Glu Glu Pro Ser Thr
145                 150                 155                 160

Leu Ser Val Leu Glu Val Ser Asp Pro Ile Thr Phe Pro Gly Leu Phe
                165                 170                 175

Gly Ser Pro Ser Ala Ser Ser Val Asn Leu Thr Asp Leu Leu Glu Lys
            180                 185                 190

Ala Gly Cys Lys Gln Phe Ala Arg Leu Ile Val Ser Ser Gly Val Val
            195                 200                 205

Lys Met Tyr Gln Ala Ala Met Asp Lys Ala Leu Thr Leu Leu Ala Pro
    210                 215                 220

Asn Asp Asp Ala Phe Lys Ala Lys Asp Leu Pro Asp Leu Ser Lys Leu
225                 230                 235                 240

Ser Ser Ala Asp Leu Val Thr Leu Leu Gln Tyr His Ala Leu Pro Gln
                245                 250                 255

Tyr Thr Pro Lys Ser Ser Leu Lys Val Ala Lys Gly Asp Ile Pro Thr
            260                 265                 270

Leu Ala Ser Thr Gly Ala Gly Lys Tyr Asp Leu Ser Val Val Ser Ser
            275                 280                 285

Gly Asp Asp Val Ser Leu Asp Thr Gly Lys Asp Lys Ser Arg Val Ala
    290                 295                 300

Ser Thr Val Leu Asp Asp Thr Pro Thr Val Ile Leu Thr Val Asp Lys
305                 310                 315                 320

Val Leu Leu Pro Pro Gly Leu Phe Gly Gly Ala Pro Ser Pro Ala Pro
                325                 330                 335

Ala Pro Gly Pro Ala Ala Asp Val Pro Ala Ser Ala Pro Ala Pro Glu
            340                 345                 350

Thr Ser Ala Pro Ala Pro Ser Pro Lys Ala Ala Gly Lys Lys Lys Lys
            355                 360                 365

Lys Ala Lys Ser Pro Ser His Ser Pro Pro Ala Pro Pro Ser Asp Ser
    370                 375                 380

Pro Asp Met Ala Pro Ala Asp Ala Pro Glu Gly Asp Ala Ala Asp Lys
385                 390                 395                 400

Val Glu Ser Lys Lys Asn Gly Ala Ala Ala Ala Ala Ser Phe Ala
                405                 410                 415

Ala Thr Gly Ala Cys Val Ala Leu Ala Val Ala Ser Phe Leu
            420                 425                 430
```

<210> SEQ ID NO 17
<211> LENGTH: 20
<212> TYPE: DNA
<213> ORGANISM: Artificial Sequence
<220> FEATURE:
<223> OTHER INFORMATION: Laboratory synthesis

<400> SEQUENCE: 17

```
gcggtcggtg gcggccatgg                                                    20

<210> SEQ ID NO 18
<211> LENGTH: 20
<212> TYPE: DNA
<213> ORGANISM: Artificial Sequence
<220> FEATURE:
<223> OTHER INFORMATION: Laboratory synthesis

<400> SEQUENCE: 18
cgcctccctc gccgtcgcgg                                                    20

<210> SEQ ID NO 19
<211> LENGTH: 17
<212> TYPE: DNA
<213> ORGANISM: Artificial Sequence
<220> FEATURE:
<223> OTHER INFORMATION: Laboratory synthesis

<400> SEQUENCE: 19
gctccggctg ttgatct                                                       17

<210> SEQ ID NO 20
<211> LENGTH: 17
<212> TYPE: DNA
<213> ORGANISM: Artificial Sequence
<220> FEATURE:
<223> OTHER INFORMATION: Laboratory synthesis

<400> SEQUENCE: 20
gcctgctctt cctcctg                                                       17

<210> SEQ ID NO 21
<211> LENGTH: 18
<212> TYPE: DNA
<213> ORGANISM: Artificial Sequence
<220> FEATURE:
<223> OTHER INFORMATION: Laboratory synthesis

<400> SEQUENCE: 21
aaacagaaag ccccaatg                                                      18

<210> SEQ ID NO 22
<211> LENGTH: 20
<212> TYPE: DNA
<213> ORGANISM: Artificial Sequence
<220> FEATURE:
<223> OTHER INFORMATION: Laboratory synthesis

<400> SEQUENCE: 22
tgccgcagta cgcgcccaag                                                    20

<210> SEQ ID NO 23
<211> LENGTH: 20
<212> TYPE: DNA
<213> ORGANISM: Artificial Sequence
<220> FEATURE:
<223> OTHER INFORMATION: Laboratory synthesis

<400> SEQUENCE: 23
ttgtccatgc cggtgtccat                                                    20

<210> SEQ ID NO 24
<211> LENGTH: 18
<212> TYPE: DNA
```

-continued

```
<213> ORGANISM: Artificial Sequence
<220> FEATURE:
<223> OTHER INFORMATION: Laboratory synthesis

<400> SEQUENCE: 24
ggtcacggca caaactca                                                    18

<210> SEQ ID NO 25
<211> LENGTH: 17
<212> TYPE: DNA
<213> ORGANISM: Artificial Sequence
<220> FEATURE:
<223> OTHER INFORMATION: Laboratory synthesis

<400> SEQUENCE: 25
gaatggcttt ccgtgtt                                                     17

<210> SEQ ID NO 26
<211> LENGTH: 17
<212> TYPE: DNA
<213> ORGANISM: Artificial Sequence
<220> FEATURE:
<223> OTHER INFORMATION: Laboratory synthesis

<400> SEQUENCE: 26
caaggtcctc ctcaacg                                                     17

<210> SEQ ID NO 27
<211> LENGTH: 75
<212> TYPE: DNA
<213> ORGANISM: Artificial Sequence
<220> FEATURE:
<223> OTHER INFORMATION: Laboratory synthesis

<400> SEQUENCE: 27
tgtcacacca caccacacaa caccaccacc gccgccagcc gccaccgacc gccgcctgct      60
cttcctcctg gccgc                                                       75

<210> SEQ ID NO 28
<211> LENGTH: 156
<212> TYPE: DNA
<213> ORGANISM: Artificial Sequence
<220> FEATURE:
<223> OTHER INFORMATION: Laboratory synthesis

<400> SEQUENCE: 28
ccgccgcctg ctcttcctcc tggccgcctc cctcgccgtc gtcggcggtg agctcccaca      60
acatcacgga catcctcgac ggctacccgg agtactcgct gtacaacagc tacctctccc     120
agaccaaggt gtgcgacgag atcaacagcc ggagca                               156

<210> SEQ ID NO 29
<211> LENGTH: 23
<212> TYPE: DNA
<213> ORGANISM: Artificial Sequence
<220> FEATURE:
<223> OTHER INFORMATION: Laboratory synthesis

<400> SEQUENCE: 29
cccgacatag atgcaataac ttc                                              23

<210> SEQ ID NO 30
<211> LENGTH: 22
<212> TYPE: DNA
<213> ORGANISM: Artificial Sequence
```

-continued

```
<220> FEATURE:
<223> OTHER INFORMATION: Laboratory synthesis

<400> SEQUENCE: 30
gcgcggtgtc atctatgtta ct                                        22

<210> SEQ ID NO 31
<211> LENGTH: 17
<212> TYPE: DNA
<213> ORGANISM: Artificial Sequence
<220> FEATURE:
<223> OTHER INFORMATION: Laboratory synthesis

<400> SEQUENCE: 31
aaacccacgc ccagaaa                                              17

<210> SEQ ID NO 32
<211> LENGTH: 17
<212> TYPE: DNA
<213> ORGANISM: Artificial Sequence
<220> FEATURE:
<223> OTHER INFORMATION: Laboratory synthesis

<400> SEQUENCE: 32
gccaggagga agagcag                                              17

<210> SEQ ID NO 33
<211> LENGTH: 17
<212> TYPE: DNA
<213> ORGANISM: Artificial Sequence
<220> FEATURE:
<223> OTHER INFORMATION: Laboratory synthesis

<400> SEQUENCE: 33
gcctgctctt cctcctg                                              17

<210> SEQ ID NO 34
<211> LENGTH: 17
<212> TYPE: DNA
<213> ORGANISM: Artificial Sequence
<220> FEATURE:
<223> OTHER INFORMATION: Laboratory synthesis

<400> SEQUENCE: 34
gtgctccggc tgttgat                                              17

<210> SEQ ID NO 35
<211> LENGTH: 24
<212> TYPE: DNA
<213> ORGANISM: Artificial Sequence
<220> FEATURE:
<223> OTHER INFORMATION: Laboratory synthesis

<400> SEQUENCE: 35
cggggtacca tggccgccac cgac                                      24

<210> SEQ ID NO 36
<211> LENGTH: 24
<212> TYPE: DNA
<213> ORGANISM: Artificial Sequence
<220> FEATURE:
<223> OTHER INFORMATION: Laboratory synthesis

<400> SEQUENCE: 36
cgcggatcct cacaagaacg acgc                                      24
```

-continued

```
<210> SEQ ID NO 37
<211> LENGTH: 33
<212> TYPE: DNA
<213> ORGANISM: Artificial Sequence
<220> FEATURE:
<223> OTHER INFORMATION: Laboratory synthesis

<400> SEQUENCE: 37
cgcgtttcga aattttgatt tcttcatcgc act                                    33

<210> SEQ ID NO 38
<211> LENGTH: 34
<212> TYPE: DNA
<213> ORGANISM: Artificial Sequence
<220> FEATURE:
<223> OTHER INFORMATION: Laboratory synthesis

<400> SEQUENCE: 38
gtcgcgatcg catgcacaac atggtgcaac agtg                                   34

<210> SEQ ID NO 39
<211> LENGTH: 23
<212> TYPE: DNA
<213> ORGANISM: Artificial Sequence
<220> FEATURE:
<223> OTHER INFORMATION: Laboratory synthesis

<400> SEQUENCE: 39
cggtacatca cggtatcaaa tcg                                               23

<210> SEQ ID NO 40
<211> LENGTH: 23
<212> TYPE: DNA
<213> ORGANISM: Artificial Sequence
<220> FEATURE:
<223> OTHER INFORMATION: Laboratory synthesis

<400> SEQUENCE: 40
taaatgctgg agcgatgcta acc                                               23

<210> SEQ ID NO 41
<211> LENGTH: 23
<212> TYPE: DNA
<213> ORGANISM: Artificial Sequence
<220> FEATURE:
<223> OTHER INFORMATION: Laboratory synthesis

<400> SEQUENCE: 41
gtgctctcca tgtcggatta tgc                                               23

<210> SEQ ID NO 42
<211> LENGTH: 24
<212> TYPE: DNA
<213> ORGANISM: Artificial Sequence
<220> FEATURE:
<223> OTHER INFORMATION: Laboratory synthesis

<400> SEQUENCE: 42
caaggcaaca agattggtta gtgg                                              24

<210> SEQ ID NO 43
<211> LENGTH: 24
<212> TYPE: DNA
<213> ORGANISM: Artificial Sequence
<220> FEATURE:
<223> OTHER INFORMATION: Laboratory synthesis
```

-continued

<400> SEQUENCE: 43
ataaaggagg agggcctcag atgg                                          24

<210> SEQ ID NO 44
<211> LENGTH: 21
<212> TYPE: DNA
<213> ORGANISM: Artificial Sequence
<220> FEATURE:
<223> OTHER INFORMATION: Laboratory synthesis

<400> SEQUENCE: 44
cacggtttgg aggttggaag c                                             21

<210> SEQ ID NO 45
<211> LENGTH: 25
<212> TYPE: DNA
<213> ORGANISM: Artificial Sequence
<220> FEATURE:
<223> OTHER INFORMATION: Laboratory synthesis

<400> SEQUENCE: 45
gcttggcatc tgcttctgtt gttgg                                         25

<210> SEQ ID NO 46
<211> LENGTH: 22
<212> TYPE: DNA
<213> ORGANISM: Artificial Sequence
<220> FEATURE:
<223> OTHER INFORMATION: Laboratory synthesis

<400> SEQUENCE: 46
ctcgctgctg atcgaggtgt cg                                            22

<210> SEQ ID NO 47
<211> LENGTH: 23
<212> TYPE: DNA
<213> ORGANISM: Artificial Sequence
<220> FEATURE:
<223> OTHER INFORMATION: Laboratory synthesis

<400> SEQUENCE: 47
atcgatgtag gtagagggac acc                                           23

<210> SEQ ID NO 48
<211> LENGTH: 22
<212> TYPE: DNA
<213> ORGANISM: Artificial Sequence
<220> FEATURE:
<223> OTHER INFORMATION: Laboratory synthesis

<400> SEQUENCE: 48
cagatctagt cgacatggtt gg                                            22

<210> SEQ ID NO 49
<211> LENGTH: 24
<212> TYPE: DNA
<213> ORGANISM: Artificial Sequence
<220> FEATURE:
<223> OTHER INFORMATION: Laboratory synthesis

<400> SEQUENCE: 49
acaccatctc tcttctttt ctat                                           24

<210> SEQ ID NO 50

-continued

```
<211> LENGTH: 23
<212> TYPE: DNA
<213> ORGANISM: Artificial Sequence
<220> FEATURE:
<223> OTHER INFORMATION: Laboratory synthesis

<400> SEQUENCE: 50
atatgggtag gtttggatat tcg                                                  23

<210> SEQ ID NO 51
<211> LENGTH: 26
<212> TYPE: DNA
<213> ORGANISM: Artificial Sequence
<220> FEATURE:
<223> OTHER INFORMATION: Laboratory synthesis

<400> SEQUENCE: 51
gtgtgtgtga gtaaaatcct agtgca                                               26

<210> SEQ ID NO 52
<211> LENGTH: 26
<212> TYPE: DNA
<213> ORGANISM: Artificial Sequence
<220> FEATURE:
<223> OTHER INFORMATION: Laboratory synthesis

<400> SEQUENCE: 52
atttgtactc ctatgtttag aatagc                                               26

<210> SEQ ID NO 53
<211> LENGTH: 31
<212> TYPE: DNA
<213> ORGANISM: Artificial Sequence
<220> FEATURE:
<223> OTHER INFORMATION: Laboratory synthesis

<400> SEQUENCE: 53
aaaaagtgtg tgtgagtaaa atcctagagc c                                         31

<210> SEQ ID NO 54
<211> LENGTH: 26
<212> TYPE: DNA
<213> ORGANISM: Artificial Sequence
<220> FEATURE:
<223> OTHER INFORMATION: Laboratory synthesis

<400> SEQUENCE: 54
acaaatatat agcaaaatcg gtgacc                                               26

<210> SEQ ID NO 55
<211> LENGTH: 25
<212> TYPE: DNA
<213> ORGANISM: Artificial Sequence
<220> FEATURE:
<223> OTHER INFORMATION: Laboratory synthesis

<400> SEQUENCE: 55
gtggttttgt ggatgttttg taact                                                25

<210> SEQ ID NO 56
<211> LENGTH: 31
<212> TYPE: DNA
<213> ORGANISM: Artificial Sequence
<220> FEATURE:
<223> OTHER INFORMATION: Laboratory synthesis

<400> SEQUENCE: 56
```

-continued

```
aaaaaacaaa tatatagcaa aatcggttac g                                      31

<210> SEQ ID NO 57
<211> LENGTH: 28
<212> TYPE: DNA
<213> ORGANISM: Artificial Sequence
<220> FEATURE:
<223> OTHER INFORMATION: Laboratory synthesis

<400> SEQUENCE: 57
aagtatttgt aatgcactat gtaaaggt                                          28

<210> SEQ ID NO 58
<211> LENGTH: 28
<212> TYPE: DNA
<213> ORGANISM: Artificial Sequence
<220> FEATURE:
<223> OTHER INFORMATION: Laboratory synthesis

<400> SEQUENCE: 58
ttaagagcac acacttccaa taatatgt                                          28

<210> SEQ ID NO 59
<211> LENGTH: 33
<212> TYPE: DNA
<213> ORGANISM: Artificial Sequence
<220> FEATURE:
<223> OTHER INFORMATION: Laboratory synthesis

<400> SEQUENCE: 59
aaaaaaagta tttgtaatgc actatgtaat ggc                                    33

<210> SEQ ID NO 60
<211> LENGTH: 25
<212> TYPE: DNA
<213> ORGANISM: Artificial Sequence
<220> FEATURE:
<223> OTHER INFORMATION: Laboratory synthesis

<400> SEQUENCE: 60
ctgggcgcgg tgcggcgggc gaggc                                             25

<210> SEQ ID NO 61
<211> LENGTH: 26
<212> TYPE: DNA
<213> ORGANISM: Artificial Sequence
<220> FEATURE:
<223> OTHER INFORMATION: Laboratory synthesis

<400> SEQUENCE: 61
ccgcctcagc gccaccgcca agctga                                            26

<210> SEQ ID NO 62
<211> LENGTH: 30
<212> TYPE: DNA
<213> ORGANISM: Artificial Sequence
<220> FEATURE:
<223> OTHER INFORMATION: Laboratory synthesis

<400> SEQUENCE: 62
aaaaactggg cgcggtgcgg cgggcgtggt                                        30

<210> SEQ ID NO 63
<211> LENGTH: 28
<212> TYPE: DNA
```

-continued

<213> ORGANISM: Artificial Sequence
<220> FEATURE:
<223> OTHER INFORMATION: Laboratory synthesis

<400> SEQUENCE: 63
aagttgtgtt tagcactatg ttattacg                                           28

<210> SEQ ID NO 64
<211> LENGTH: 28
<212> TYPE: DNA
<213> ORGANISM: Artificial Sequence
<220> FEATURE:
<223> OTHER INFORMATION: Laboratory synthesis

<400> SEQUENCE: 64
tttagcataa taactactat tcatcatt                                           28

<210> SEQ ID NO 65
<211> LENGTH: 33
<212> TYPE: DNA
<213> ORGANISM: Artificial Sequence
<220> FEATURE:
<223> OTHER INFORMATION: Laboratory synthesis

<400> SEQUENCE: 65
aaaaaaagtt gtgtttagca ctatgttatg aca                                     33

<210> SEQ ID NO 66
<211> LENGTH: 26
<212> TYPE: DNA
<213> ORGANISM: Artificial Sequence
<220> FEATURE:
<223> OTHER INFORMATION: Laboratory synthesis

<400> SEQUENCE: 66
gcaggagaca cttggtgccg cctctc                                             26

<210> SEQ ID NO 67
<211> LENGTH: 28
<212> TYPE: DNA
<213> ORGANISM: Artificial Sequence
<220> FEATURE:
<223> OTHER INFORMATION: Laboratory synthesis

<400> SEQUENCE: 67
gcagattatt ttcggtgggt cccgtctc                                           28

<210> SEQ ID NO 68
<211> LENGTH: 31
<212> TYPE: DNA
<213> ORGANISM: Artificial Sequence
<220> FEATURE:
<223> OTHER INFORMATION: Laboratory synthesis

<400> SEQUENCE: 68
aaaaagcagg agacacttgg tgccgccact t                                       31

<210> SEQ ID NO 69
<211> LENGTH: 1296
<212> TYPE: DNA
<213> ORGANISM: Artificial Sequence
<220> FEATURE:
<223> OTHER INFORMATION: Laboratory synthesis

<400> SEQUENCE: 69
atggccgcca ccgaccgccg cctgctcttc ctcctggccg cctccctcgc cgtcgcggcg        60

-continued

```
gtcagctccc acaacatcac ggacatcctc gacggctacc cggagtactc gctgtacaac    120
agctacctct cccagaccaa ggtgtgcgac gagatcaaca gccggagcac ggtcacctgc    180
ctcgtgctca ccaacggcgc catgtcctcc ctcgtctcca acctctccct cgccgacatc    240
aagaacgcgc tccgcctcct caccctcctc gactactacg acaccaagaa gctgcactcc    300
ctcagcgacg gctccgagct caccaccacg ctgtaccaga ccaccggcga cgcctccggt    360
aacatgggcc acgtcaacat caccaacctg cgcggcggca aggttgggtt cgcctccgcc    420
gcgcccggct ccaagttcca ggccacctac accaagtccg tcaagcagga gccgtacaac    480
ctctccgttc ttgaggtctc cgaccccatc accttccccg gcctcttcga ctccccgtcg    540
gccgcgtcga ccaacctcac cgcgcttctt gagaaggccg ggtgcaagca gttcgcgcgg    600
ctcatcgtgt cgtccggggt gatgaagatg taccaggcgg ccatggacaa ggcgctgacg    660
ctgttcgcgc ccaacgacga cgcgttccag gccaagggcc tgccggatct gagcaagctg    720
accagcgccg agctggtgac gcttctgcag taccacgcct tgccgcagta cgcgcccaag    780
gcgtcgctca agaccatcaa gggccacatc cagaccctgg cctccaccgg agcgggtaag    840
tacgacctct ccgtcgtcac taagggcgac gacgtgtcca tggacaccgg catggacaag    900
tcccgcgtcg cgtccaccgt gctggacgac accccgacgg ttatccacac ggtggacagc    960
gtgctgctgc cgccagagct cttcggtggc gcaccttccc ccgcgccggc gcccggaccg   1020
gcaagcgatg tgccagccgc ttctcccgcg ccagaaggct cctcgccggc gccctccccc   1080
aaggcggcgg gcaagaagaa aaagaagggc aagtcgcctt cccattcccc acccgcgcct   1140
ccggccgaca cgcctgacat gtcgcccgcc gacgcgcccg cgggagaaga ggctgcagac   1200
aaagccgaga agaagaacgg cgccaccgcg gcggccacga gtgttgcggc cactgtggcc   1260
tccgccgccg ctctgctcgc cgcgtcgttc ttgtga                             1296
```